United States Patent [19]

Imbach et al.

[11] Patent Number: 4,476,301

[45] Date of Patent: Oct. 9, 1984

[54] OLIGONUCLEOTIDES, A PROCESS FOR PREPARING THE SAME AND THEIR APPLICATION AS MEDIATORS OF THE ACTION OF INTERFERON

[75] Inventors: Jean-Louis Imbach; Gilles J. M. Gosselin, both of Montpellier, France

[73] Assignee: Centre National de la Recherche Scientifique, Paris, France

[21] Appl. No.: 390,878

[22] Filed: Jun. 22, 1982

[30] Foreign Application Priority Data

Apr. 29, 1982 [GB] United Kingdom ............... 8212458

[51] Int. Cl.³ ..................... C07H 15/12; C07H 17/00
[52] U.S. Cl. ....................................... 536/27; 536/28; 536/29
[58] Field of Search .............................. 536/27, 28, 29

[56] References Cited

U.S. PATENT DOCUMENTS 3,444,158  5/1969  Honjo et al. ........................ 536/28
3,520,872  7/1970  Wechter ............................... 536/28
4,378,352  3/1983  Imbach et al. ...................... 536/27

OTHER PUBLICATIONS

Chem. Abstract 96:163091b (1982) (Tetrahedron Lett. 1981, 22 (47), 4699–4702).
Journal of Biological Chemistry, vol. 256, No. 7, pp. 3253–3257 (1981).
Baglioni, "Interferon Induced Enzymatic Activities and Their Role in the Antiviral State", Cell 17, 1979, pp. 255–264.
Kerr et al., "An Inhibitor of Protein Synthesis Synthesized With an Enzyme Fraction from Interferon Treated Cells", PNAS 75, p. 256–260 (1978).

Primary Examiner—Ethel G. Love
Attorney, Agent, or Firm—Fleit, Jacobson, Cohn & Price

[57] ABSTRACT

The invention relates to new oligonucleotides, a process for preparing the same and their application as mediators of the action of interferon.

7 Claims, 1 Drawing Figure

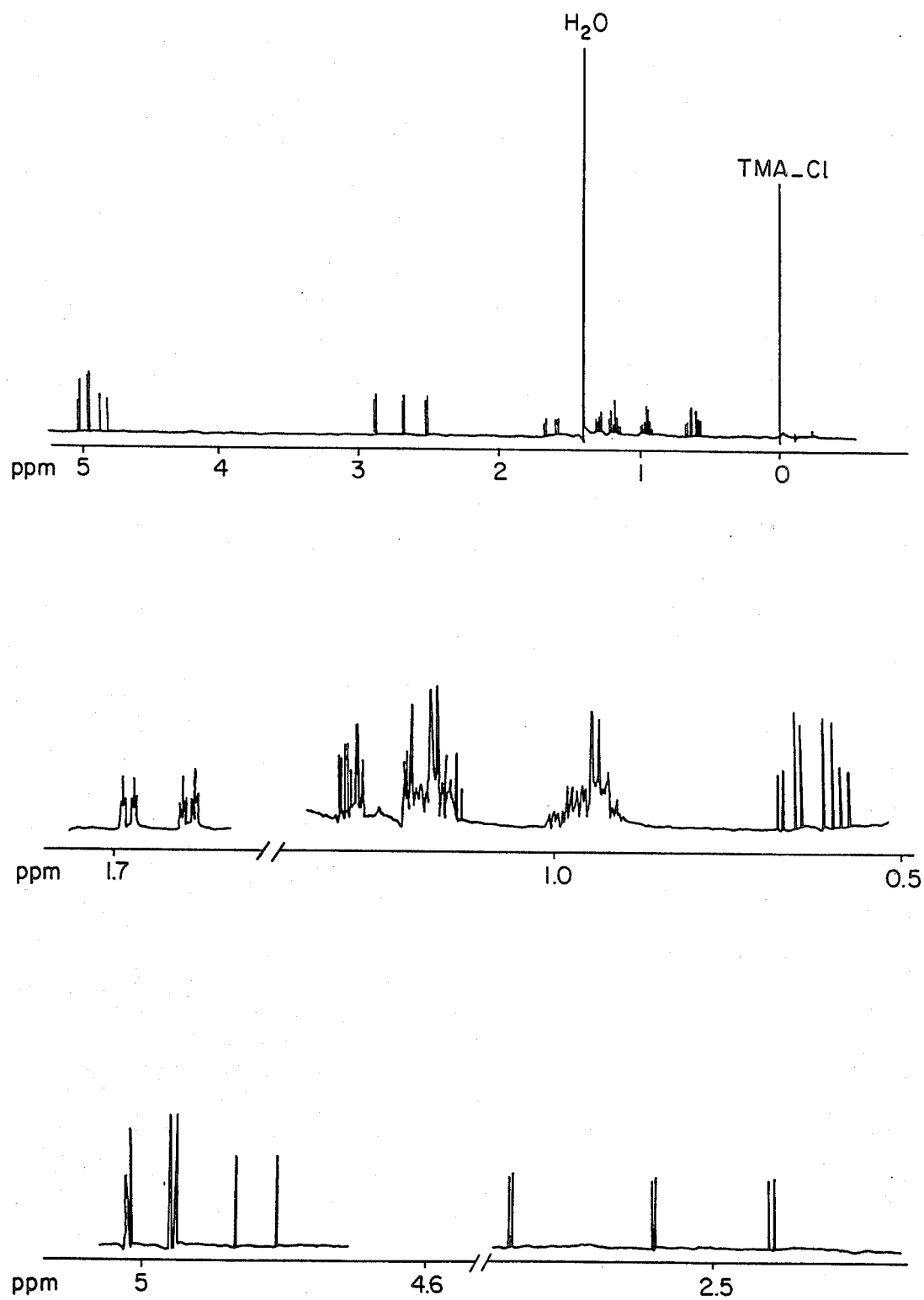
FIG. I

OLIGONUCLEOTIDES, A PROCESS FOR PREPARING THE SAME AND THEIR APPLICATION AS MEDIATORS OF THE ACTION OF INTERFERON

BACKGROUND OF THE INVENTION

Interferon is known to be a family of related proteins characterized notably by antiviral activities.

It has been observed that the antiviral action of interferon is mediated by the synthesis of specific proteins. Specific assays for these proteins have allowed to identify the function of two of them, both enzymes (Baglioni C., 1979, Interferon induced enzymatic activities and their role in the antiviral state, Cell 17, 255-64). One of these enzymes is an oligonucleotide polymerase. This oligonucleotide polymerase forms from ATP short chains of adenosines linked by 2'→5' phosphodiester bonds (Kerr I. M. and Brown R. E., 1978, pppA2'p-5'A2'p5'A: An inhibitor of protein synthesis synthesized with an enzyme fraction from interferon treated cells, PNAS 75, 256-60), which have been designated by 2'-5' oligoadenylates. One of these 2',5' oligoadenylates can be represented by the following formula:

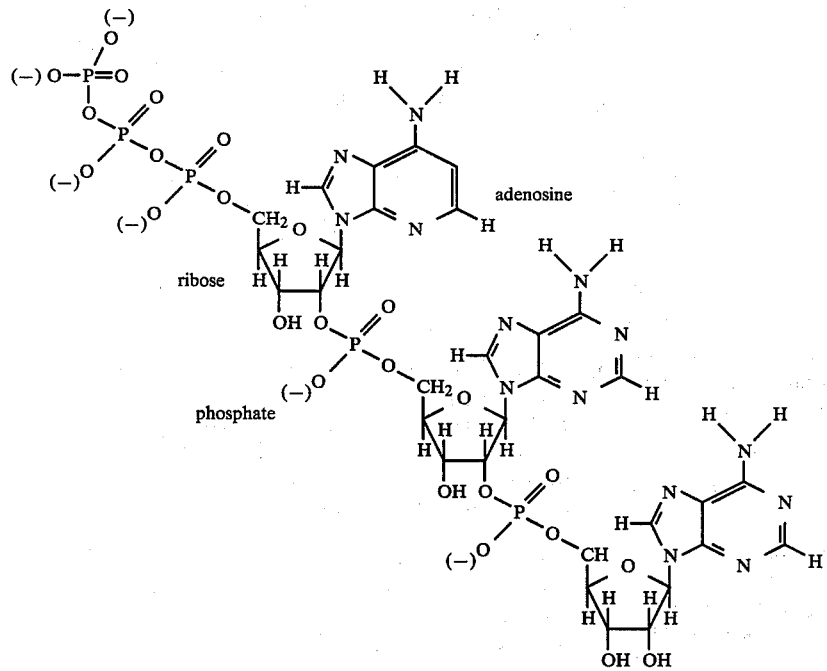

It is composed of short chains containing several adenosine groups (adenine+ribose), linked with one another by 2'-5' phosphodiester bonds, as shown and in which the 5' position of the adenine nucleus of the terminal adenosine is linked to a various number of phosphate groups (up to three on the above represented 2'→5' oligoadenylate). When the above represented 2'→5' oligoadenylate is entirely dephosphorylated, that is when the phosphate group linked to the 5' position of the adenine nucleus of the terminal adenosine is freed from said various number of phosphate groups, the resulting compound is designated by "(2'→5')A₃core", which is an abbreviation for "riboadenylyl (2'→5')riboadenylyl 2'→5')riboadenosine core". It will be understood that the expression "2'-5' oligoadenylate" as mentioned above and as used hereafter shall, as a matter of convenience of language, be understood as also including the partially dephosphorylated or entirely dephosphorylated, i.e. the (2'→5')A₃ core.

It must be pointed out that in the following of the description, all the chemical compounds are designated under the French chemical nomenclature.

The discovery of these 2'-5' oligoadenylates revealed a new class of biologically active oligonucleotides deemed to have an important role as mediators of the action of interferon, notably in the activation of endoribonuclease which is present as well in interferon treated cells as in interferon non treated cells, and in the inhibition of protein synthesis. But the 2'→5'phosphodiester bonds of these adenylates are rapidly cleaved by the enzyme 2'-phosphodiesterase (cf. the reference above mentioned to Baglioni C.).

Both endoribonuclease and 2'-phosphodiesterase are present in about the same amount in untreated cells as in cells treated with interferon.

When the cell is treated with interferon, the concentration of 2'-5' oligonucleotide polymerase which recognizes endoribonuclease and which interacts with viral replicative structures, increases.

When interferon is removed from the culture medium, the 2'-5' oligonucleotide polymerase activity declines and the cell loses its antiviral state.

The synthesis of proteins induced by interferon is transitory and therefore cells kept in tissue culture do not maintain enhanced levels of these proteins.

Researches have been undertaken to find synthetic analogs of 2'-5' oligoadenylates with increased activity compared to the activity of 2'-5' oligoadenylates induced in cells treated with interferon (Baglioni C. et al., 1981, Analogs of (2'-5')oligo(A). Endonuclease activation and inhibition of protein synthesis in intact cells, The Journal of Biological Chemistry, vol. 256, no. 7, p. 3 253-3 257).

It is to be pointed out that all the analogs which have been synthesized resort to modifications of the riboadenosine unit, for most of them, or to the use of arabinoadenosine.

The results obtained so far, with respect to enzymatic stability, for analogs of 2'-5' adenylates, constituted by chains containing several riboadenosines or of arabinoadenosines have allowed to define some of the structural requirements for endonuclease activation and inhibition of protein synthesis.

The conclusion which has been drawn so far, on the basis of the studies carried out on analogs of 2'-5' adenylates containing riboadenosine units is a mere hypothesis according to which some analogs of 2'-5' adenylates, in the riboadenosine series, could be responsible for some of the same effects (with respect to inhibition of protein synthesis) as the ones induced by interferon.

Applicants have now found new oligonucleotides having a structure different from that of the natural 2'-5' oligoadenylates and its known analogs having an interferon like activity, an increased duration of biological activity, a resistance to degradation by 2'-phosphodiesterase and a higher degree of protection.

It is thus an object of the invention to provide new oligonucleotides which can be recognized by the endoribonuclease, i.e. which can build up with endoribonuclease, an active complex.

It is another object of the invention to provide new oligonucleotides which are more resistant to degradation by 2'-phosphodiesterase.

It is also an object of the invention to provide new oligonucleotides which have an activity like interferon with increased duration of the biological activity.

These objects are achieved by new oligonucleotides according to the invention, which comprise a chain containing in turn n identical or different nucleosidic units, n being higher than 1, among which at least one is constituted by xyloadenosine, these nucleosidic units being linked by a 2'→5' bond comprising a linking group containing at least one phosphorus atom.

These objects are preferably achieved by new oligonucleotides according to the invention, which comprise a chain containing in turn n identical or different nucleosidic units, n being higher than 1, among which at least one is constituted by xyloadenosine, these nucleosidic units being linked by a 2'→5' bond comprising a linking group containing at least one phosphorus atom.

A nucleosidic unit designates a compound constituted by a pentose linked to a puric or pyrimidic base, in which the pentose can be in the pyrane or furane form. In the following, the formulae will represent the pentoses in their furane form, but the scope of the invention also relates to oligonucleotides in which the pentoses are in the pyrane form, i.e. of formula:

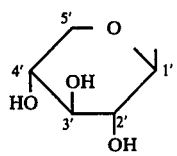

Xyloadenosine designates the compound constituted by xylose linked to adenine and can be represented by the following formula:

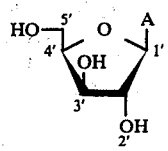

in which the xylose is in the furane form but can also be in the pyrane form and in which A represents adenine.

In the framework of the invention, adenine designates the molecule represented by the following formula:

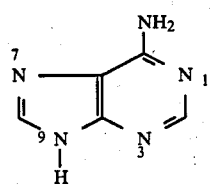

It is to be underlined, in the following description, that, according to its position in the oligonucleotides according to the invention, xyloadenosine represents the following radical, which also enables to define the meaning of "linked by 2'→5' bond".

When xyloadenosine is contained in a terminal group, hereafter termed as "first" nucleosidic unit of the oligonucleotide, it may be in the form of the radical denoted by formula:

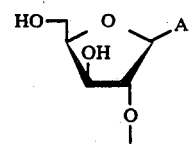

This representation means that the oxygen atom of the 2' hydroxyl group of the xyloadenosine (when it is the first nucleosidic unit of the oligonucleotide according to the invention) is engaged in a bond comprising at least one phosphorus atom, said bond being linked to the oxygen of the 5' hydroxyl group of the second nucleosidic unit.

When xyloadenosine is contained in the opposite end part of the oligonucleotide concerned, i.e. in the "last" nucleosidic unit of the oligonucleotide, it shall normally be in the form of a radical of formula:

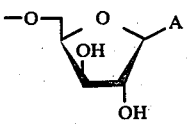

This representation means that the oxygen atom of the 5' hydroxyl group of the xyloadenosine (when it is the last nucleosidic unit of the oligonucleotide according to the invention) is engaged in a bond comprising at least one phosphorus atom, said bond being linked to the oxygen of the 2' hydroxyl group of the penultimate nucleosidic unit.

When xyloadenosine is neither the first, nor the last unit of the oligonucleotide, it designates the radical of formula:

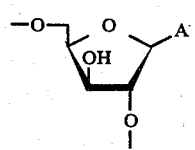

This representation means that the oxygen atom of the 5' hydroxyl group of the xyloadenosine is engaged in a bond comprising at least one phosphorus atom with the oxygenation of the 2' hydroxyl group of the preceding nucleosidic unit in the oligonucleotide of the invention, and that the oxygen atom of the 2' hydroxyl group of the xyloadenosine is engaged in a bond comprising at least one phosphorus atom with the oxygen atom of the 5' hydroxyl group of the following nucleosidic unit in the oligonucleotide of the invention.

The number of nucleosidic units constituting the oligonucleotides of the invention is not limited in the upper values, to the extent the oligonucleotides obtained are soluble in a physiologically acceptable liquid vehicle. This number may however be limited in practice, to the extent where the increase of said number and the corresponding more difficult synthesis would not be warranted by a corresponding sufficient increase of activity. The number of nucleosidic units may be chosen, so that molecular weight of the oligonucleotides of the invention should be preferably comprised in the range of from 800 to 3,500.

In a preferred class of oligonucleotides according to the invention, the value of n is not higher than 10, and is preferably of 7 or 8.

Oligonucleotides in which the value of n is 3 or 4 are particularly preferred.

In the oligonucleotides of the invention, the first nucleosidic unit and/or the last nucleosidic unit can be linked to one or more phosphate groups.

In a preferred class of oligonucleotides according to the invention, the first nucleosidic unit is linked to one or more phosphate groups.

Preferably, the number of these phosphate groups is from 1 to 3.

These phosphate groups can be separated by one or more methylene groups, preferably by one to 3 methylene groups.

In a preferred class of oligonucleotides according to the invention, the first nucleosidic unit is linked to the following phosphate groups:

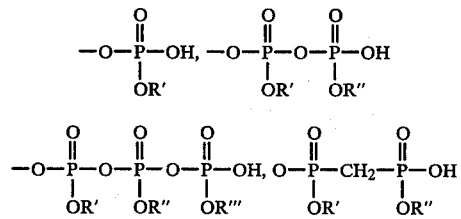

in which R', R'', R''' represent, independently from each other:
an hydrogen atom,
an alkyl radical having from 1 to 4 carbon atoms, particularly methyl radical,
an ethyl radical substituted in beta position by a cyano, aryl or arylsulfonyl group,
an aryl radical substituted or not by an halogen atom or a nitro group,
a trihalogenoethyl radical.

In a preferred class of oligonucleotides according to the invention, the 2'→5' bond linking two nucleosidic units and comprising at least one phosphorus atom is a phosphodiester bond, a phosphotriester bond, an alkylphosphonate bond.

The 2'→5' phosphodiester bond, linking two adjacent nucleosidic units in the oligonucleotides of the invention can be represented as follows (it being understood that the part of nuclei shown below as well as in relation to subsequent examples of bonds, belong to the corresponding nucleosides):

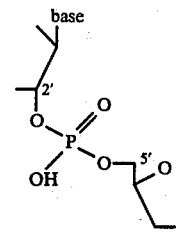

The 2'→5' phosphotriester bond, linking two adjacent nucleosidic units in the oligonucleotides of the invention can be represented as follows:

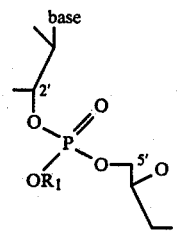

in which $R_1$ represents an alkyl radical having from 1 to 4 carbon atoms, particularly a methyl,
an ethyl radical substituted in beta position by a cyano aryl or arylsulfonyl group,
an aryl radical substituted or not by an halogen atom or a nitro group,
a trihalogenoethyl radical.

The 2'→5' phosphonate bond, linking two adjacent nucleosidic units in the oligonucleotide according to the invention can be represented as follows:

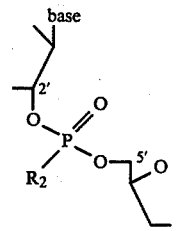

in which $R_2$ can represent an alkyl having from 1 to 4 carbon atoms, particularly a methyl.

Preferred oligonucleotides according to the invention comprise n identical or different nucleosidic units derived from adenine, among which one is constituted by xyloadenosine.

A further preferred group of oligonucleotides according to the invention, comprises n identical or different nucleosidic units derived from adenine, among which one is constituted by xyloadenosine, said nucleosidic units derived from adenines being engaged in 2'→5' phosphodiester bonds or phosphotriester bonds.

In another class of oligonucleotides according to the invention, the last nucleosidic unit is a desoxy-2' nucleosidic unit derived from adenine or a desoxy-3' nucleosidic unit derived from adenine or a desoxy-2', 3' nucleosidic residue derived from adenine.

In a preferred class of oligonucleotides according to the invention, the last nucleosidic unit is chosen from among:
desoxy-2'-ribofurannosyl-adenine,
desoxy-2'-xylofurannosyl-adenine,
desoxy-2', 3'-ribofurannosyl-adenine,
desoxy-2'-ribopyrannosyl-adenine,
desoxy-2'-xylopyrannosyl-adenine,
desoxy-2', 3'-ribopyrannosyl-adenine.

In another preferred class of oligonucleotides according to the invention, or subclasses among the preferred classes above mentioned, the hydroxyl group in 3' of at least one of the nucleosidic units alkylated, by an alkyl having from 1 to 10 carbon atoms, preferably methylated.

In further preferred classes of compounds according to the invention, one nucleosidic unit is xyloadenosine and the (n−1) other nucleosidic units derived from adenine are chosen from among:
riboadenosine,
arabinoadenosine,
xyloadenosine,
lyxoadenosine.

Particular subclasses of preferred compounds among said last mentioned "further class" are those in which the hydroxyl group in 3' of at least one of the nucleosidic units is alkylated, by an alkyl having from 1 to 10 carbon atoms, preferably methylated.

In additional preferred classes at least one of the nucleosidic units is selected from among:
desoxy-3' riboadenosine,
desoxy-3' arabinoadenosine, In a particular class of compounds of the invention, preferred oligonucleotides according to the invention comprise one D-β-xylofurannosyl-9-adenine of formula:

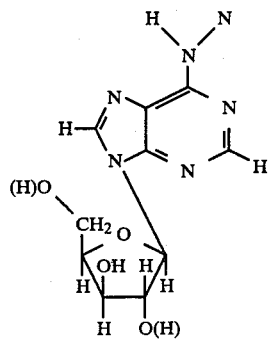

and the remaining (n−1) nucleosidic units derived from adenine are chosen from among:
ribofurannosyl-adenine,
arabinofurannosyl-adenine,
xylofurannosyl-adenine,
lyxofurannosyl-adenine,
ribopyrannosyl-adenine,
arabinopyrannosyl-adenine,
xylopyrannosyl-adenine,
lyxopyrannosyl-adenine,
desoxy-3'-ribofurannosyl-adenine,
desoxy-3'-arabinofurannosyl-adenine,
desoxy-3'-ribopyrannosyl-adenine,
desoxy-3'-arabinopyrannosyl-adenine.

In another class of oligonucleotides according to the invention, at least one nucleosidic unit is xylopyrannosyladenine and the remaining (n−1) nucleosidic units derived from adenine are chosen from among:
ribofurannosyl-adenine,
arabinofurannosyl-adenine,
xylofurannosyl-adenine,
lyxofurannosyl-adenine,
ribopyrannosyl-adenine,
arabinopyrannosyl-adenine,
xylopyrannosyl-adenine,
lyxopyrannosyl-adenine,
desoxy-3'-ribofurannosyl-adenine,
desoxy-3'-arabinofurannosyl-adenine,
desoxy-3'-ribopyrannosyl-adenine,
desoxy-3'-arabinopyrannosyl-adenine, It is understood that the invention also relates to preferred classes or subclasses belonging to the last mentioned class of oligonucleotides containing said at least one xylopyrannosyl adenine, and in which any of the other (n−1) nucleosidic units may consist of nucleosidic units different from those derived from adenine, particularly any of those defined in relation to the above mentioned selected preferred classes or sub-classes.

Generally speaking, the invention also relates to any class of compounds including several of the features defined in relation to said above mentioned "another" "further", "particular" . . . preferred classes or subclasses according to any possible combination of corresponding selected nucleosides.

For instance, supplementary preferred subclasses may consist of oligonucleotides in which:
the last nucleosidic units correspond to those which have more specifically defined in the mentioned preferred classes;
and other nucleosidic units correspond to any of those specifically defined in said "further preferred", "particular" classes of compounds which were defined.

A particularly preferred class of oligonucleotides according to the invention are the oligonucleotides of formula:

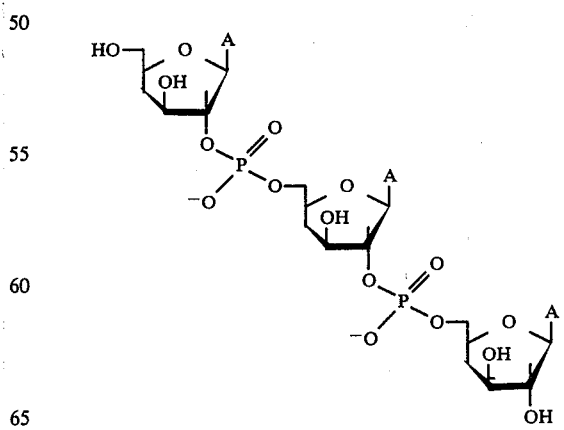

which will be hereafter designated by xyloadenylyl (2'→5')xyloadenylyl (2'→5')xyloadenosine, in which A represents adenine or a derivative thereof as above defined.

The invention also relates to the salts which can be obtained by reacting said oligonucleotides with suitable bases, particularly quaternary ammonium salts, such as triethylammonium, and its inorganic salts, such as sodium salt.

More generally, preferred compounds according to the invention may also be defined by the following general formula or structure:

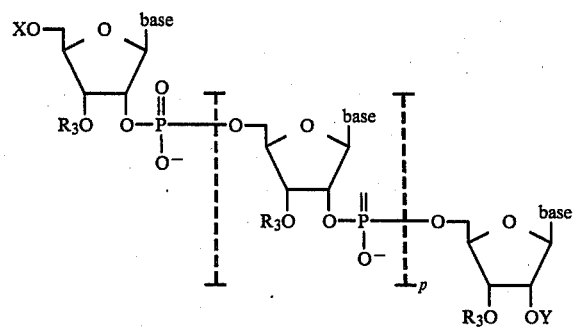

it being understood that any of the osidic group may be replaced in the above said formula by:
 a corresponding 3'-desoxy group or
 a 2'-desoxy group or a 2', 3'-desoxy group as concerns, the last of the nucleotides in said formula, and wherein:
each of the

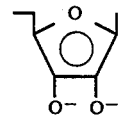

is any osidic group, particularly any of the osidic or desoxy-osidic group herein contemplated;
p is (n-2), n being as herein defined;
X is either $R_5$ as herein defined, or hydrogen, or a mono- or polyphosphate as herein defined;
Y is either $R_2$ as herein defined, identical or different to $R_5$, or hydrogen, or a mono- or polyphosphate group as herein defined;
"base" means a purine or pyrimidine base, preferably adenine;
$R_3$, either the same or different from one osidic or desoxy-osidic group to another, identical to or different from $R_2$ or $R_5$, is as herein defined, or hydrogen;
and wherein at least one of the nucleosidic units in said formula comprise a xylo-adenosine or desoxy-xyloadenosine unit.

In the above said formula, phosphodiester-, phosphotriester-, alkylphosphonate bonds may be substituted for the phosphate bonds or linkages shown.

"As herein defined" makes references to any of the groups referred in any part of the disclosure in the corresponding location of the formula.

The invention further relates to a process for preparing the oligonucleotides of the invention, particularly according to three alternatives of chemical synthesis, each of which is liable to be carried out either in solid phase or in liquid phase. The most commonly technique is the one in liquid phase.

The main characteristics of each of the three approaches are hereunder explained.

Phosphodiester method

The process of the invention, according to a first alternative, comprises, starting from nucleosides or nucleotides including one or several groups:

designating any of the osidic groups contemplated hereabove, and more particularly ribose, arabinose, xylose, lyxose, desoxy-3' ribose, desoxy-3' arabinose, and for the last osidic group as above defined designating more particularly ribose, arabinose, xylose, lyxose, desoxy-3' ribose, desoxy-3' arabinose, desoxy-2' ribose, desoxy-2' xylose, desoxy-2', 3' ribose, reacting a first compound with a second compound in the presence of an activation agent, -wherein said first compound comprises either a nucleotidic unit of structure ②:

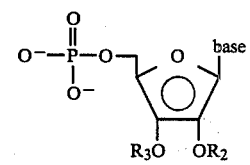

or the corresponding desoxy-3' unit; in which the 5' carbon is linked to a $PO_4$--group, the 2' hydroxyl group is protected by a protection group $R_2$ and in which the optional 3' hydroxyl group is protected by a protection group $R_3$, -wherein said second compound comprises either a nucleosidic unit of structure ①:

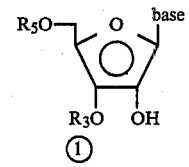

or the corresponding desoxy-3' unit, in which the 5' hydroxyl group is protected by a protection group $R_5$ and the optional 3' hydroxyl group is protected by a protection group $R_3$, and
wherein said activation agent is selected from among those which enable the phosphate group of the nucleotidic unit ② of said first compound to provide for a condensation with the 2'-hydroxyl group of the nucleosidic unit of said second compound to thereby obtain the third compound ①-② of structure:

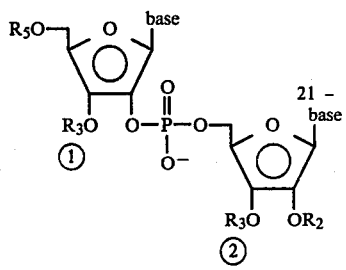

which is then further reacted, after preliminary selective deprotection, either at the level of $R_5$ or of $R_2$, with either of the first case (after deprotection at the level of $R_5$) with a fourth compound which comprises either a nucleotidic unit of structure ③:

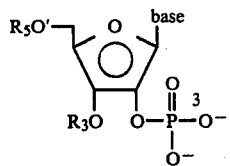

or the corresponding desoxy-3' unit, in which the 2' carbon is linked to a $PO_4^{--}$group, and in which the 5' carbon is protected by a protection group $R_5$ and the optional 3' hydroxyl group is protected by a protection group $R_3$, in the presence of an activating agent selected from among those which enable the phosphate group of the nucleotidic unit ③ of said fourth compound to provide for a condensation with the 5' hydroxyl group of the nucleotidic unit of said third compound, to thereby obtain a compound of structure ③-①-②:

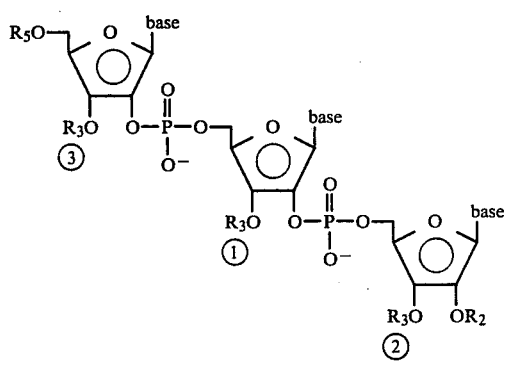

or in the second case (after deprotection at the level of $R_2$) with a fifth compound either identical to said first compound or comprising, a distinct nucleotidic unit of structure ②:

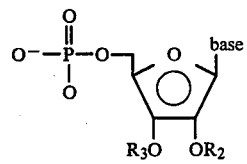

to thereby obtain a compound of structure ①-②-②:

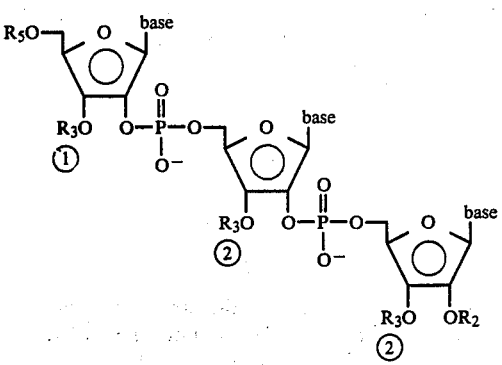

these steps being optionally further repeated if a tetramer or even greater oligomer are sought, with the proviso that at least one of the:

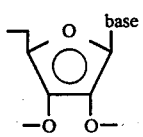

shall be xyloadenosine.

For example, the further repetition of the part of the process as defined for making the trimer would yield a tetramer representable either by:

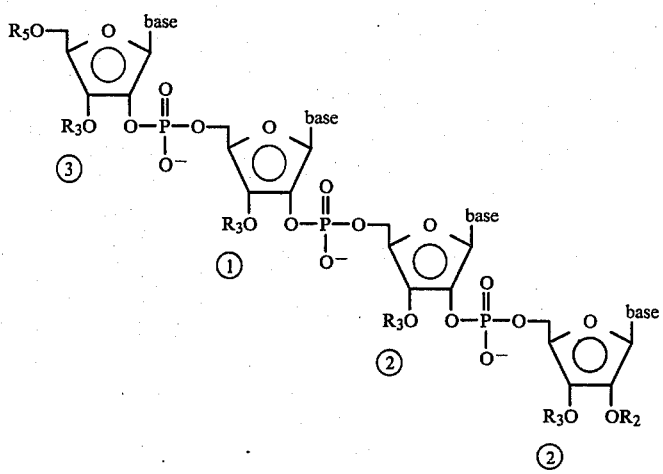

or:

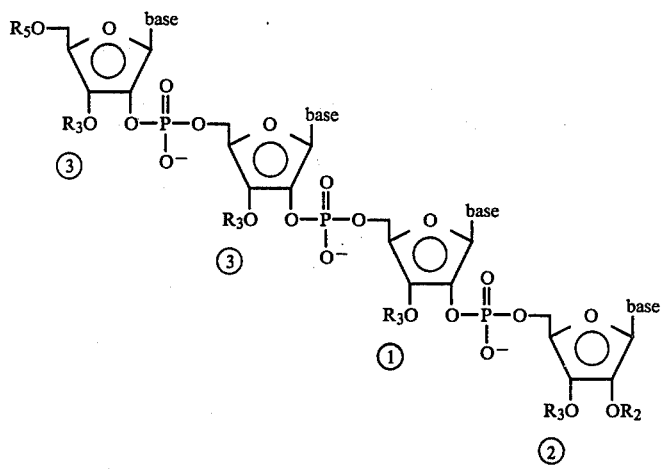

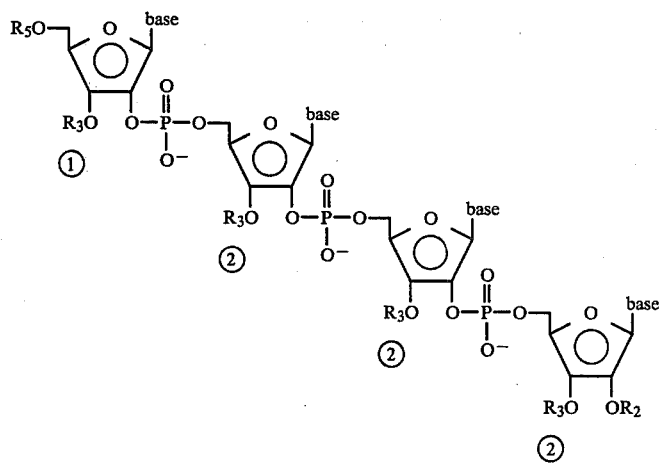

Other alternatives for preparing oligonucleotides according to the invention consist in reacting one nucleotide or nucleoside with a previously formed oligomer or reacting a previously prepared oligomer with another previously prepared oligomer.

Concerning the above mentioned protective, $R_2$ and $R_3$ are baso labile groups and represent particularly acyl groups having from 2 to 4 carbon atoms, preferably acetyl groups or benzyl groups;

$R_5$ is an acido labile group and represents particularly a trityl derivative such as monomethoxytrityle.

Concerning the activation agents, they preferably are chosen from among arylsulfonyl chlorides, particularly mesitylene sulfonyl chloride.

Alternatively, the phosphodiester method can also be carried out in the same way as above described, by reaction of said first compound comprising the nucleotidic unit of structure ② yet comprising a $PO_4^{--}$ group on the 2' carbon (instead of the 5' carbon) with a second compound comprising a nucleosidic unit of structure ①, in which the 5' hydroxyl group is condensed with the phosphate group of the nucleotidic unit ②.

The diagram hereunder is given as an illustration:

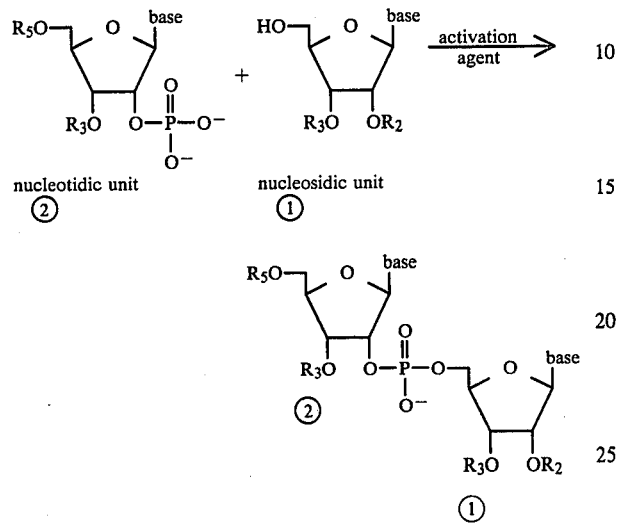

By way of example, the phosphodiester method can be carried out according to what is described by P. T. GILHAM and H. G. KHORANA, in J. Amer. Chem. Soc. 1958, 80, 6 212.

Phosphotriester method

The second process of the invention, according to a second alternative consists in resorting to any of the alternaitves described under the phosphodiester method, yet in which the $PO_4{}^{--}$ group is replaced by the:

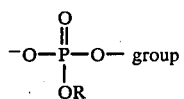 group

Consequently, the process of the invention according to a second alternative comprises, starting from nucleosides or nucleotides including one or several groups:

designating any of the osidic groups contemplated hereabove, reacting a first compound with a second compound in the presence of an activation agent, wherein said first compound comprises either a nucleotidic unit of structure ②:

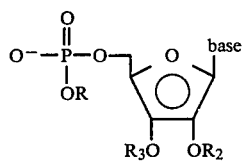

or the corresponding desoxy-3' unit; in which the 5' carbon is linked to a $PO_4R^-$ group, the 2' hydroxyl group is protected by a protection group $R_2$ and in which the optional 3' hydroxyl group is protected by a protection group $R_3$;

wherein said second compund comprises either a nucleosidic unit of structure 1 :

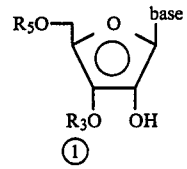

or the corresponding desoxy-3' unit, in which the 5' hydroxyl group is protected by a protection group $R_5$ and the optional 3' hydroxyl group is protected by a protection group $R_3$, and wherein said activation agent is selected from amoung those which enable the phosphate group of the nucleotidic unit ② of said first compound to provide for a condensation with the 2'-hydroxyl group of the nucleosidic unit of said second compound to thereby obtain the third compound ①-② of structure:

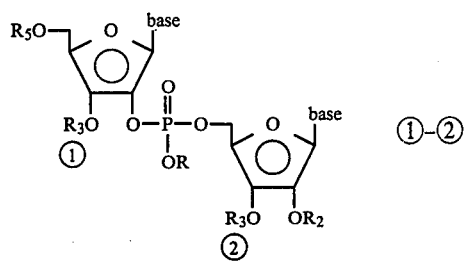

which is then further reacted, after preliminary selective deprotection, eitehr at the level of $R_5$ or of $R_2$, with either in the first case (after deprotection at the level of $R_5$) wth a fourth compound which comprises either a nucleotidic unit of structure ③:

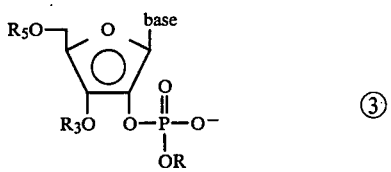

or the corresponding desoxy-3' unit, in which the 2' carbon is linked to a $PO_4R^-$ group, and in which the 5' carbon is protected by a protection group $R_5$ and the optional 3' hydroxyl group is protected by a protection group $R_3$, in the presence of an activating agent selected from among those which enable the phosphate group of the nucleotidic unit ③ of said fourth compound to provide for a condensation with the 5' hydroxyl group of the nucleotidic unit of said third compound, to thereby obtain a compound of structure ③-①-②:

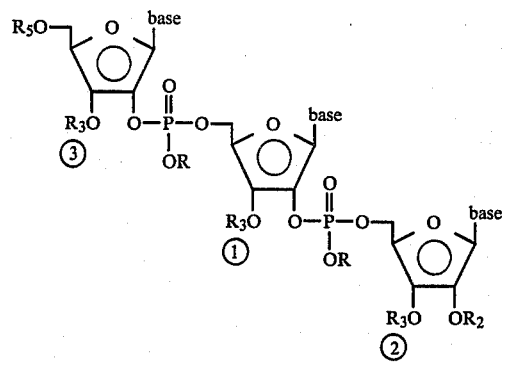

or in the second case (after deprotection at the level of $R_2$) with a fifth compound either identical to said first compound or comprising, a distinct nucleotidic unit of structure ②:

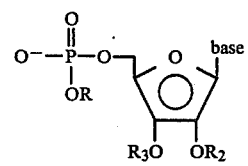

to thereby obtain a compound of structure ①-②-②:

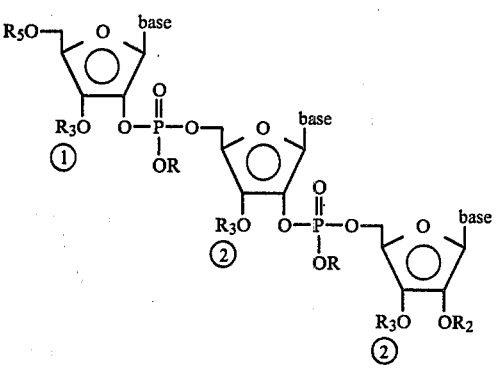

these steps being optionally further repeated if a tetramer or even greater oligomer are sought, with the proviso that at least one of the:

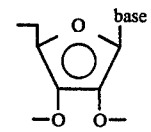

shall be a xyloadenosine.

For example, the further repetition of the part of the process as defined for making the trimer would yield a tetramer representable either by:

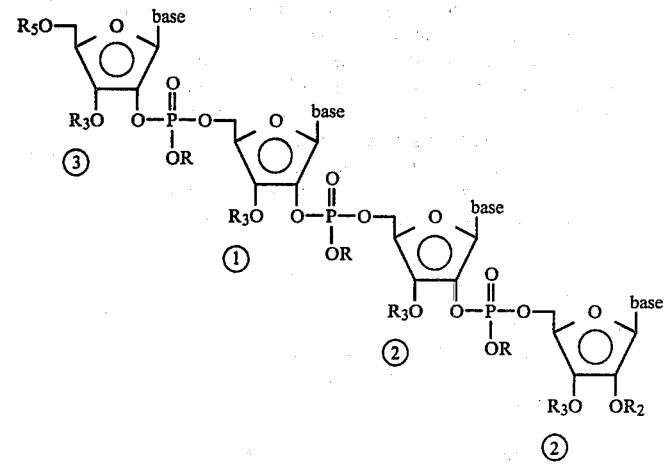

or:

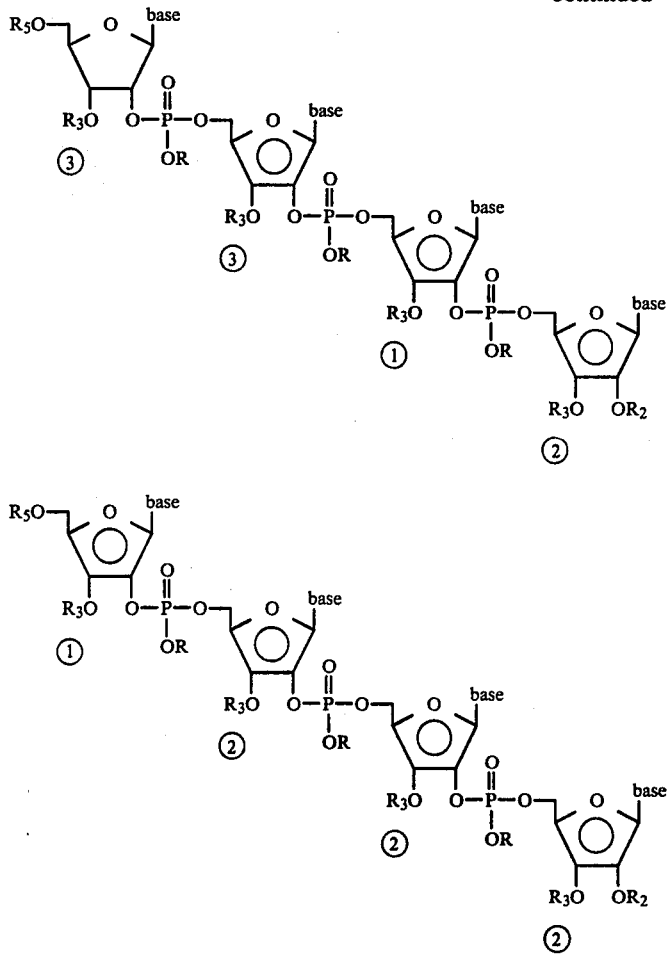

Other alternatives for preparing oligonucleotides according to the invention consist in reacting one nucleotide or nucleoside with a previously formed oligomer or reacting a previously prepared oligomer with another previously prepared oligomer.

Concerning the above mentioned protective groups, $R_2$ and $R_3$ are baso labile groups and represent particularly acyl groups having from 2 to 4 carbon atoms, preferably acetyl groups or benzoyl groups; $R_5$ is an acido labile group, and represents particularly a trityl derivative such as monomethoxytrityle.

Concerning the activation agents, they preferably are chosen from among arylsulfonates of heterocycles containing a nitrogen atom, said aryl group being substituted or not by an alkyl group having from 1 to 3 carbon atoms, particularly methyl or isopropyl, said heterocycles being particularly chosen from among imidazole, triazole, tetrazole substituted by a nitro group.

Concerning the $PO_4R^-$ group, R represents an alkyl radical having from 1 to 4 carbon atoms, particularly methyl radical, an ethyl radical substituted in beta position by a cyano, aryl or arylsulfonyl group, an aryl radical substituted or not by an halogen atom or a nitro group, a trihalogenoethyl radical.

Alternatively, the phosphotriester method can also be carried out in the same way as above described, by reaction of said first compound comprising the nucleotidic unit of structure ②, yet comprising a $PO_4R^-$ group on the 2' carbon (instead of the 5'0 carbon) with a second compound comprising a nucleosidic unit of structure ①, in which the 5' hydroxyl group is condensed with the phosphate group of the nucleotidic unit ②.

The diagram hereunder is given as an illustration:

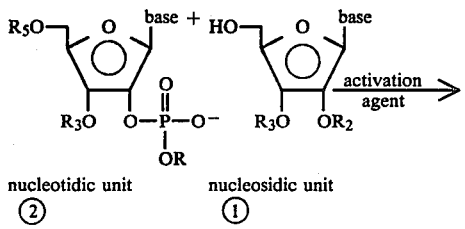

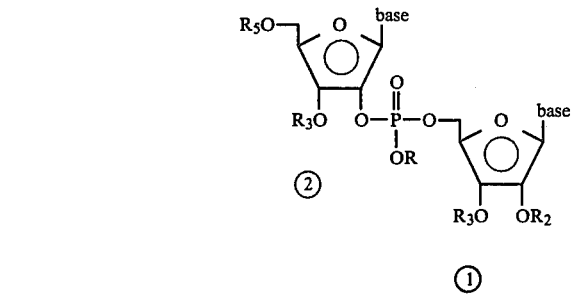

By way of example, the phosphotriester method can be carried out according to A. M. MICHELSON and A. R. TODD, J. Chem. Soc., 1955, 2 632 and K. ITAKURA et al. Can. J. Chem., 1973, 51, 3 649.

The advantages of the phosphotriester method is that the triester bonds are non ionic, which makes easier isolation and purification of the intermediate compounds obtained during the synthesis. On the contrary in the phosphodiester method, the phosphodiester bonds are ionic, which can be responsible for a insolubility of intermediate compouns in most conventional organic solvents, thereby making the isolation an purification of said intermediate compounds more difficult, when resorting to chemical methods of extraction and purification; moreover the presence of the intermediate fragments of nucleophile phosphodiester function can be responsible, after activation, by the activation agents, for chain breaking.

Phosphite method

The process of the invention, according to a third alternative, comprises, starting from nucleosides or nucleotides incluing one or severla groups

designating any of the osidic groups contemplated hereabove, reacting a first compound with a second compound, in the absence of an activation agent, wherein said first compoun comprises either a nucleotide unit of structure ①

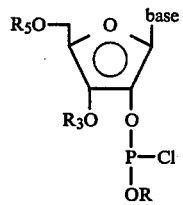

or the corresponding desoxy-3' unit; in which the 5' carbon is linked to a $PO_2RCl$ group, the optional 3' hydroxyl group is protected by a protection group $R_3$ wherein said second compound comprises either a nucleosidic unit of structure ②

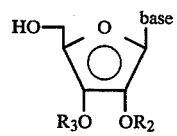

of the corresponding desoxy-3' unit, in which the 2' hydroxyl group is protected by a protection group $R_2$ and the optional 3' hydroxyl group is protected by a protection group $R_3$ thereby obtaining a third compound ①-② of structure

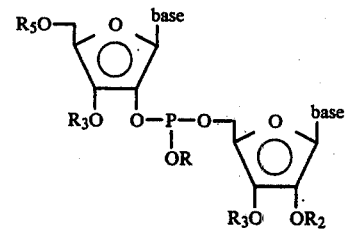

then oxydizing said compound ①-②, obtain a fourth compound ③ of structure:

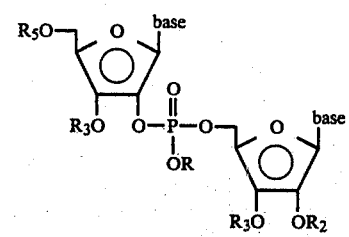

with the proviso that at least one of the:

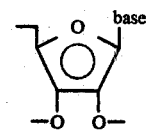

shall be a xyloadenosine.

Concerning the reaction of compound ① with compound ②, it is carried out in the presence of a solvent such as pyridine.

Concerning oxydation of compond ①-② into compound ③, it is carried out with an oxydation agent such as $I_2$ or peroxyde derivative, particularly perbenzoic acid.

The oxydation is advantageously carried out with $I_2/H_2O/THF$.

Concerning the protection groups above mentioned:
$R_2$ and $R_3$ represent baso labile groups and paticularly acyl groups having from 1 to 4 carbon atoms, preferably acetyl groups, or benzoyl groups;

$R_5$ represents an acido labile group, particularly a trityl derivative, such as monomethoxytrityle.

concerning $PO_2RCl$, R represents an aryl group substituted by an halogen atom, such as orthochlorophenyl.

By way of example, this method can be carried out according to R. L. LETSINGER et al., J. Amer. Chem. Soc., 1975, 97, 3 278.

According to a preferred process for preparing the oligonucleotides of the invention, one resorts to the phosphotriester method, by using appropriate protective groups. In order to avoid side reactions, in oligonucleotidic synthesis, it is necessary to protect all the nucloephile functions, except the function which are involved in the formation of the desired internucleotidic bond The following example will enable to understand the invention, without limiting it.

This example relates to the synthesis of xyloadenylyl (2'→5')-xylo-adenylyl (2'→5') xyloadenosine.

The preparation of the trimer of β-D xylofurannosyladenine with (2'→5')internucleotidic bonds in the form of its triethylammonium salt of following formula

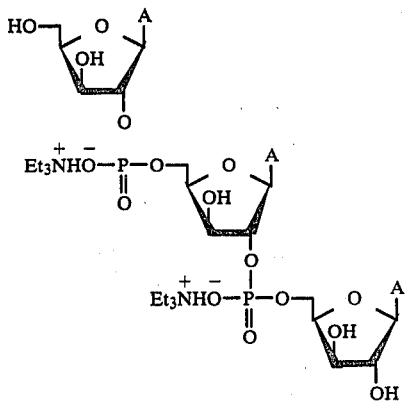

is carried out as follows or in an equivalent manner.

The abbreviations which are hereafter used have the following meaning:

mMTr      monomethoxytrityl group

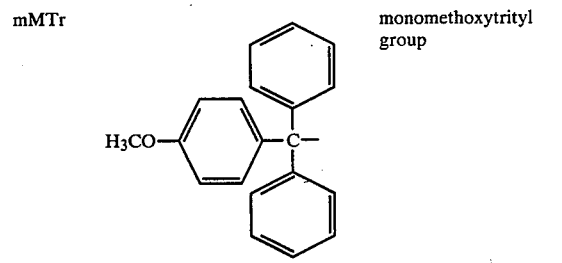

Bz      benzoyl group

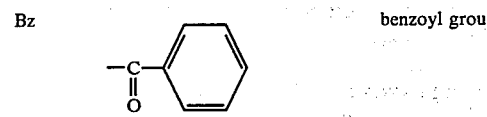

TBDMS      tertiobutyldimethyl-silyl group

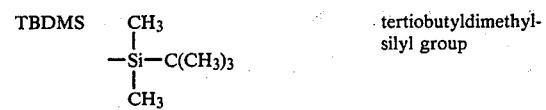

oClPh      orthochlorophenyl

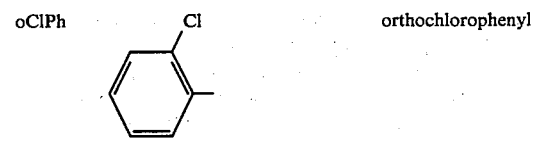

The compound of the following formula 22

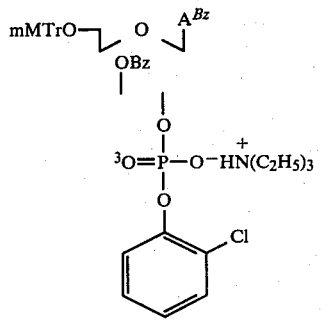

in which mMTr is an acido labile group an Bz is a baso labile group is reacted on to the compound of the following formula 2:

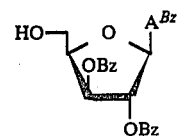

The compound obtained has the following formula 23

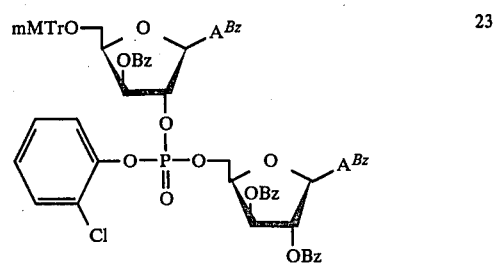

and then the 5' hydroxyl function of compound 23 is deprotected, to give the compound of formula 24:

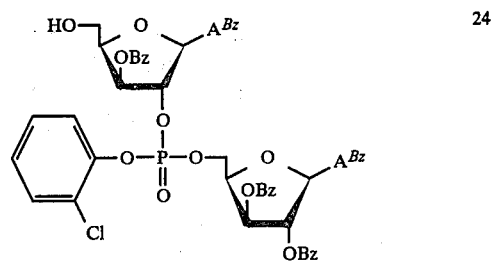

which is reacted with the compoun of formula 22 to give the compound of formula 28

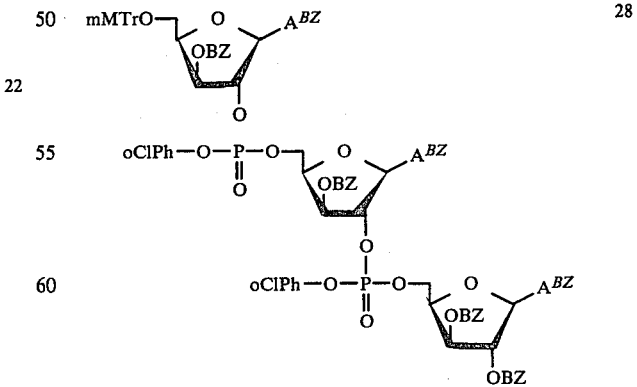

which is transformed into the compound of formula 29

The compond of formula 22

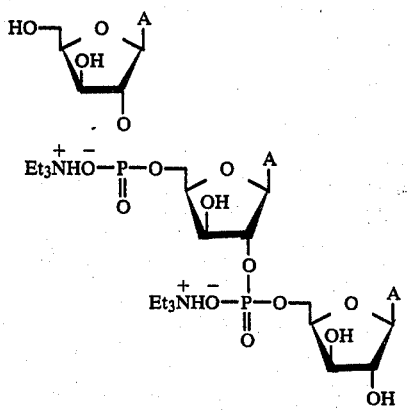

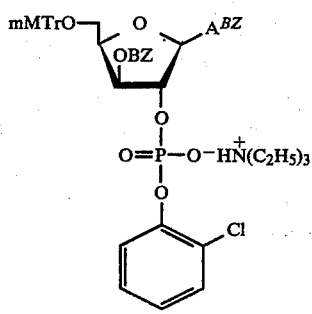

can be obtained from the compound of formula:

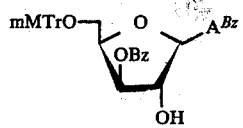

by reacting ortho-chlorophenylphosphorodi-(triazol-1,2,4-ide) in excess for instance in an acetonitrile-pyridine mixture further treated with aqueous triethylamine.

The compound of formula 2:

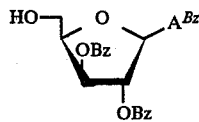

can be obtained from the compound of formula 1

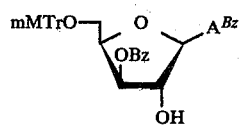

which is benzoylated, for instance with benzoic anhydrid in pyridine to give the compound of formula 20

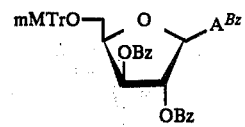

which is then transformed by treatment for instance with p-toluene sulfonic acid in a mixture of chloroformemethanol, into the compound of formula 2.

In a practical way, for the synthesis of xylo adenylyl (2'→5') xyloadenylyl (2'→5') xyloadenosine, one resorts to the compound of formula 1:

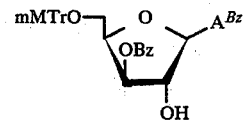

Preparation of the compound of formula (1)

The starting material is di-O-benzoyl-3,5,0-isopropylidene-1,2α-D-xylofurannose of formula 5

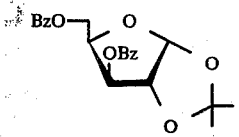

which can be obtained quickly with a good yield from D-xylose (B. R. BAKER and R. E. SCHAUB - J. Amer. Chem. Soc. 1955, 77, 5900).

By acetolyse of compound of formula 5, the di-O-benzoyl-3,5 di-O-acetyl-1,2-D-xylofurannose of formula 11 is obtained according to the following diagram:

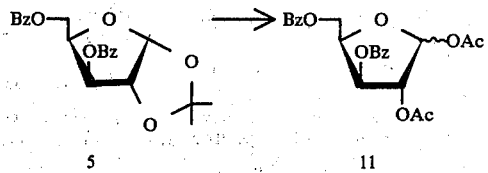

Note:
Ac represents the —C—CH$_3$ group
              ||
              O

The reaction of the compound of formula 11 with adenine in acetonitrile, in presence of stannous tetrachloride, gives after treatment and purification the compound of formula 12 with a yield of 70%.

On the one hand, the compound of formula 12 is totally desacylated by a solution of sodium methylate in methanol to give β-D-xylofurannosyl-9-adenine 13.

On the other hand, a selective reaction of desacetylation by hydrazine in a mixture of acetic acid and pyridine gives compound 14, which is non substituted in the 2' position.

The following diagram illustrates the above described reactions:

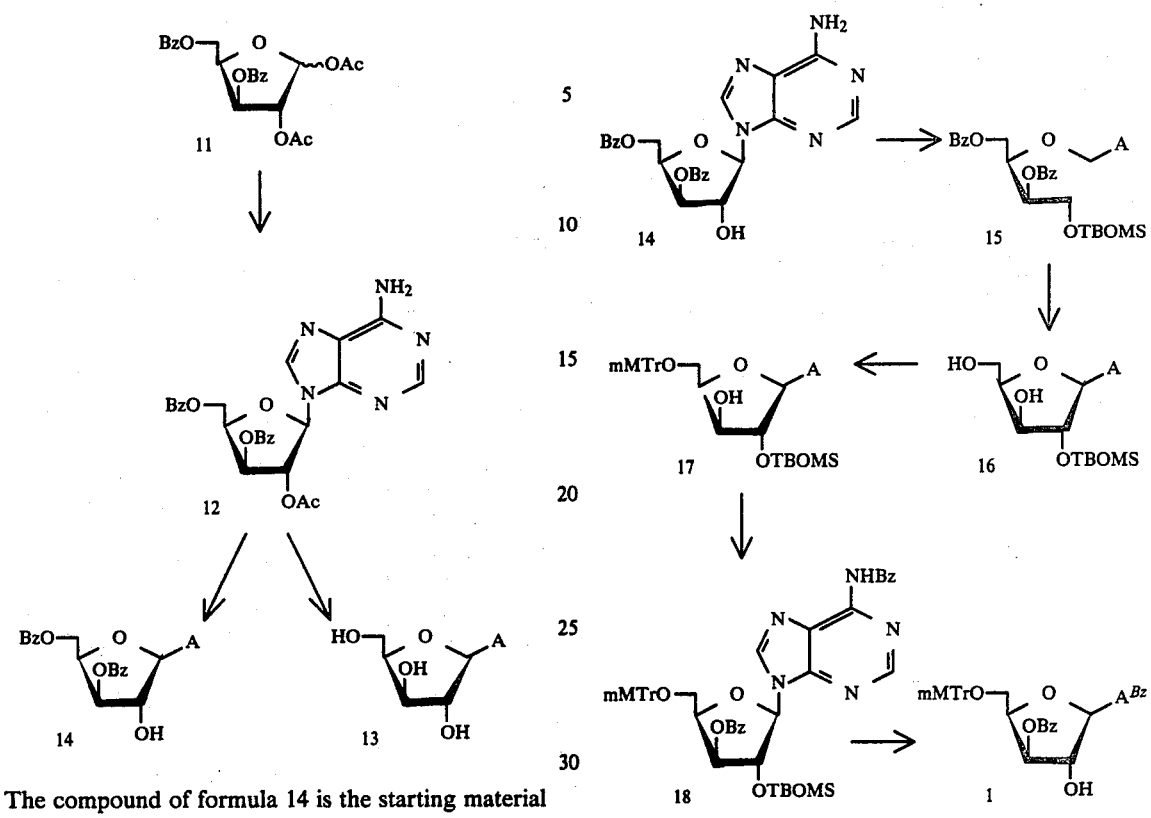

The compound of formula 14 is the starting material for the synthesis of the desired compound of formula 1.

The free 2'-hydroxyl group of compound 14 is protected, in a first step, by a tertiobutyldimethylsilyl group according to the conventional method (K. K. OGILVIE & D. J. IWACHA - Tetrahedron Lett., 1973, 317) (K. K. OGILVIE, A. L. SCHIFMAN & C. L. PENNEY, Can. J. Chem. 1979, 57,2230).

The resulting derivative 15 is then debenzoylated to give 0-tertiobutyldimethylsilyl-2' β-D-xylofurannosyl-9 adenine 16. The yield is of about 41%.

In the following step, the primary alcohol function of compound 16 is specifically protected by monomethoxytritylation to give compound 17.

The following step involves the simultaneous protection of the exocyclic amine function of adenine and of the 3'-hydroxyle of xylose by benzoyl groups.

Thus benzoylation of compound 17 by benzoic anhydride in pyridine (J. F. M. de ROAIJ et al., Recl. Trav. Chim. Pays-Bas, 1979, 98, 537) gives derivative 18 which has a benzoyl group on the heterocycle.

In a last step, the compound 18 is readily and selectively desilylated by tetrabutylammonium fluoride (K. K. OGILVIE & D. J. IWACHA - Tetrahedron Lett., 1973, 317) (K. K. OGILVIE, A. L. SCHIFMAN & C. L. PENNEY, Can. J. Chem. 1979, 57, 2230) which enables to obtain the desired compound of formula 1.

The following diagram illustrates the above described reaction:

From compound 1, the compound of formula 2 can be obtained.

In a first step, a benzoylation of 1, with benzoic anhydride in pyridine gives the fully protected compound 20. This compound 20 can also be synthesized from β-xylofurannosyl-adenine 13.

But the transformation of compound 13 into 20 successively involves a selective monomethoxytritylation of the primary hydroxyl, then a benzoylation of the remaining functions.

The deblocking of the monomethoxytrityl group of 20 is carried out by treating this compound by a solution of 2% p-toluenesulfonic acid in a mixture of chloroform-methanol (H. TAKAKU et al. J. Org. Chem., 1980, 45, 3 347) and enables to obtain the desired compound 2.

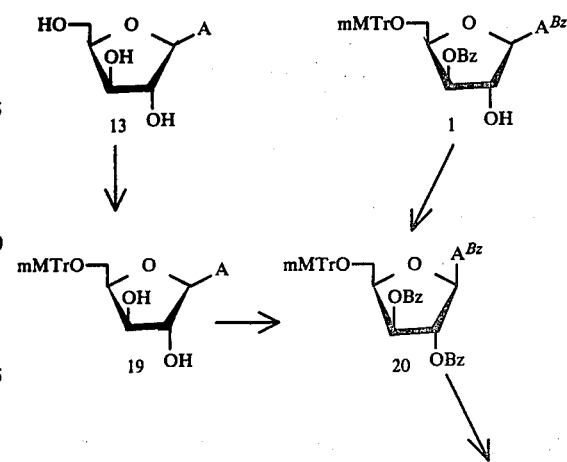

-continued

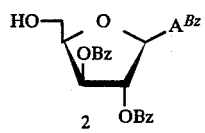

Synthesis of the trimer of β-D-xylofurannosyl-9-adenine with (2'→5') internucleotidic bonds The phosphotriester approach requires two distinct steps of phosphorylation. The first step consists in synthesizing the 2'-phosphodiester derivative from compound 1. The second step consists in reacting this phosphodiester intermediate compound on to the 5'-hydroxyl function of compound 2 (or of the dimer which has been intermediarily obtained) in the presence of an activation agent.

Synthesis of 2'-arylphosphate derivative 22

It is advantageous to resort to ortho-chlorophenyl groups to protect internucleotidic phosphates (W. T. MARKIEWICZ et al., Nucleic Acids Res., Symposium Series, No 7, 1980, 115 and C. B. REESE et al., Tetrahedron Lett., 1978, 2 727).

A relationship between the attractive character of the protective group and the reactivity of phosphate, when the internucleotidic bond occurs, has been established. In this respect, chlorophenyl groups have been found out as being superior over other less electronegative groups used so far, such as β-cyanoethyl and trichloro-2,2,2-ethyl.

Moreover, the efficiency and selectivity of oximate ions for the final deprotection of internucleotidic phosphates has been established, because these ions do not involve chain breaking (C. B. REESE et al. Tetrahedron Lett.n 1978, 2 727).

Thus the reaction of compound 1 with an excess of o-chlorophenylphosphorodi-(triazol-1,2,4 ide) 21 (J. B. CHATTOPADHYAYA et al., Tetrahedron Lett., 1979, 5 059 and J. B. CHATTOPADHYAYA et al., Nucleic Acids Res., 1980, 8, 2 039) prepared in situ in a mixture of acetonitrile-pyridine, gives after treatment with aqueous triethylamine, the compound 22. This latter is isolated in the form of its triethylammonium salt with a very good yield, by extraction with chloroform and precipitation in petrolatum.

The following diagram illustrates the above described reaction:

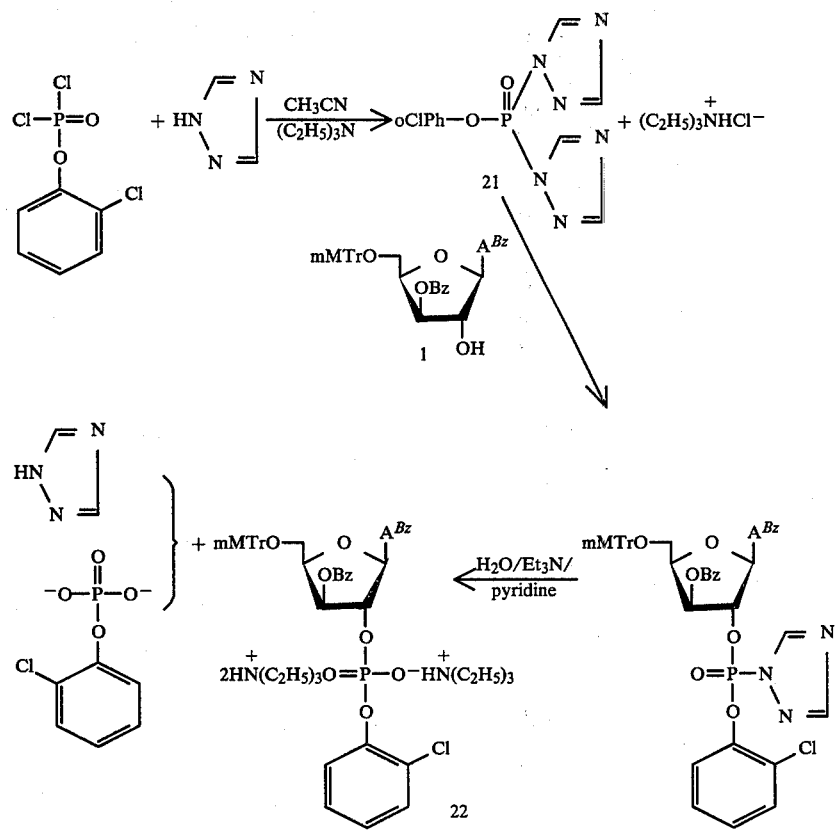

Synthesis of the totally protected trimer 28

When reacting phosphodiester nucleosidic 22 on to the 5'-hydroxyl group of compound 2 or of dimeric compound 24, it is advantageous to resort to mesitylene-sulfonyl-1-nitro-3-triazole-1,2,4 (which will be hereafter referred to as MSNT), as activation agent, because of its stability and efficiency.

Thus a solution in pyridine of 22 and 2 (which is slightly in excess) is treated by 2,9 eq of MSNT, during 20 minutes, at room temperature.

The reaction mixture is then poured into an aqueous solution saturated with sodium bicarbonate and is extracted with chloroform.

The monophosphate dinucleoside 23 thus obtained, is directly treated by 2% p-toluenesulfonic acid in a mixture of $CHCl_3/CH_3OH$ to give detritylated dimer 24;

this latter is isolated with a yield of 70% with respect to compound 2, after neutralisation, extraction and purification on silica column and precipitation within petrolatum.

A last reaction between the dimeric compound 24 presenting a free 5'-hydroxyl group and phosphodiester 22, followed by an appropriate treatment, enables to isolate, after chromatography on a silica column and precipitation within petrolatum, the totally blocked trimer 28, in the form of a white powder, with a yield of 75%.

The following diagram illustrates the above described reaction:

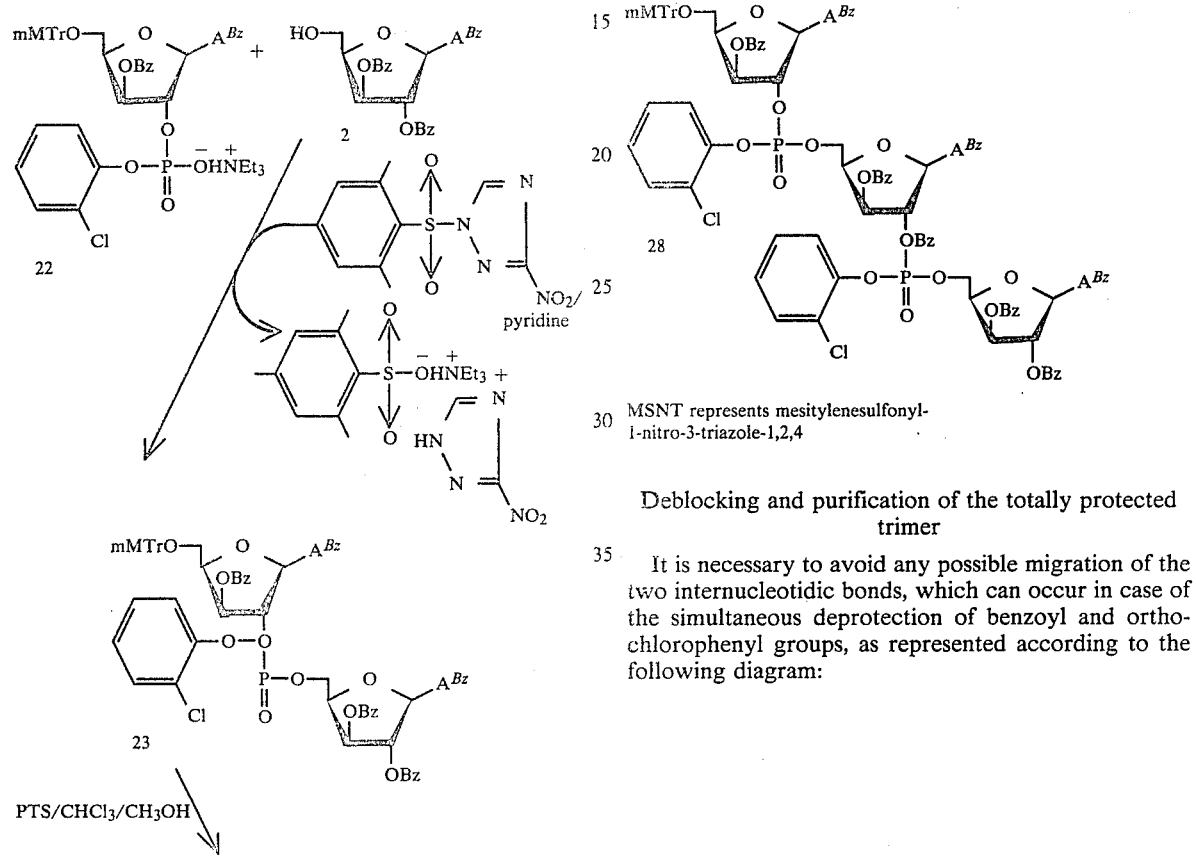

MSNT represents mesitylenesulfonyl-1-nitro-3-triazole-1,2,4

Deblocking and purification of the totally protected trimer

It is necessary to avoid any possible migration of the two internucleotidic bonds, which can occur in case of the simultaneous deprotection of benzoyl and ortho-chlorophenyl groups, as represented according to the following diagram:

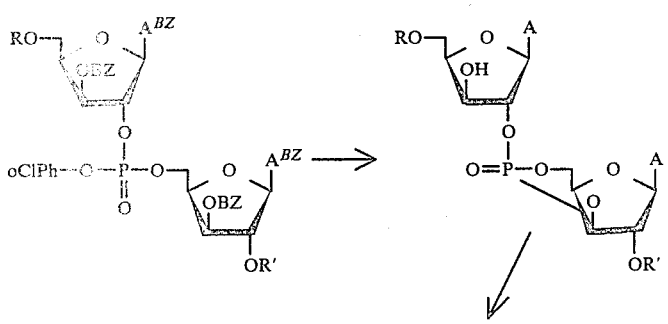

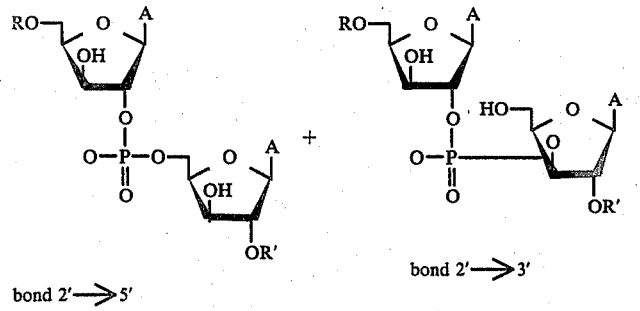

bond 2'⟶5' bond 2'⟶3'

(C. B. Reese, Tetrahedron, 1978, 34, 31443)

Consequently, to obtain compound 28, with no possible migration of the two internucleotidic bonds, the following steps are carried out in the following order: 1° the totally protected trimer 28 is treated by p-nitrobenzaldoximate of tetramethylguanidinium (C. B. REESE et al., Tetrahedron Lett., 1978, 2 727 and S. S. JONES et al., Tetrahedron, 1980, 36, 3 075) in order to eliminate the o-chlorophenyl groups, which protect phosphate groups.

The following diagram illustrates this reaction:

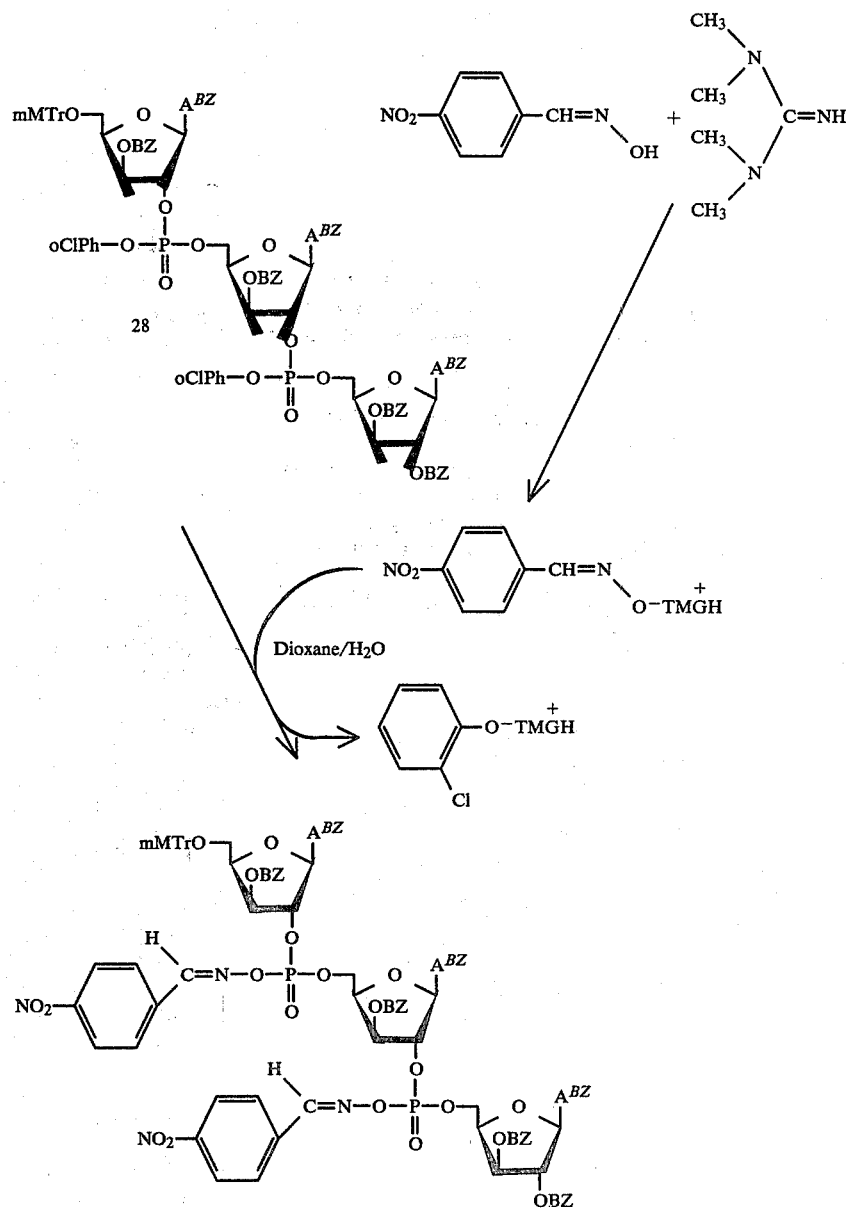

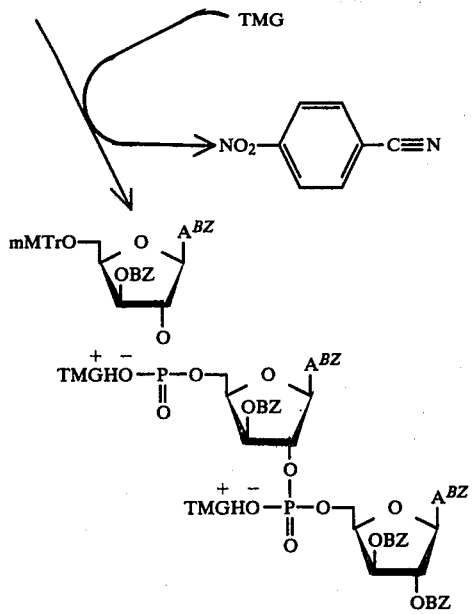

note:
TMG represents tetramethylguanidinium

2° Aqueous ammoniac (20%) is then added to hydrolyse the O- and N-benzoyl groups; the temperature is of about 40° C. and the reaction time is of about 20 hours.

2° In order to eliminate methoxytrityle, the compound is then placed in 80% acetic medium, for about 4 hours at about 25° C.

4° Then the extraction is carried out and the compound 29 is obtained in the form of its triethylammonium salt, by means of a chromatography on a Sephadex DEAE-25 column with a yield higher than 80%.

The following diagram illustrates the four different steps above described:

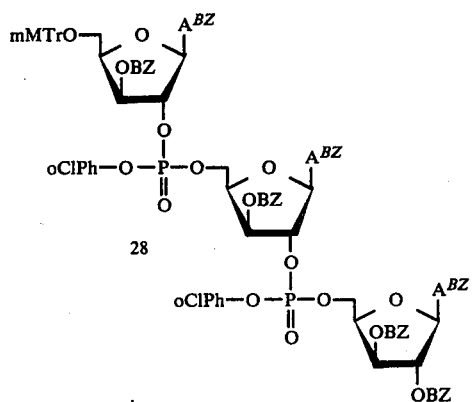

(1) nitro-4 benzaldoxime/TMG
(2) 20% aqueous NH₄OH, 40° C., 20 h.
(3) 80% aqueous CH₃COOH, 25° C., 4 h.
(4) extraction, then Sephadex DEAE-A25

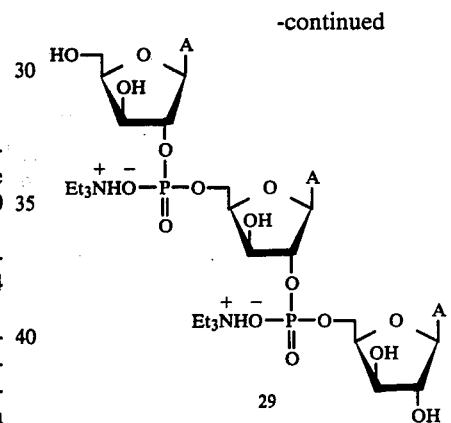

The following part relates to the preparation of compound 29 according to the invention, and is given as an example which is in no way limitative.

The general indications are the same as the ones already mentioned, except when it is specifically precised.

Additional indications to be specified are the following ones:

the spectra of phosphore NMR have been recorded on a spectrometer of the type of the one commercialized under BRUCKER WP 80, working at MHz 32.37, the chemical shiftings are expressed in δ ppm, with respect to the orthophosphoric acid, taken as an external reference;

the H.P.L.C. system consists of Waters material: U₆K injector, 6 000 A and M-45 pumps, m 720 programmer, UV 440 to 254 nm detector, refractometer detector R-401 and M-730 computer-recorder;

the spectrophotometric purity controls of xyloadenyl-(2'→5') xyloadenylyl-(2'→5')-xyloadenosine, as well as those of enzymatic digestions of same trimer have been carried by thin layer chromatography (hereinafter referred to as ccm), and then by HPLC analysis on Waters μ Bondapack C₁₈ (30 cm) analytic column; the elution gradient is formed from a A solution (12% of acetonitril) and from a B solution (12% of acetonitrile), each of them being prepared in a 1% aqueous solution of ammonium acetate at a pH of 5.9, according to G. D. Mc FARLAND and P. M. BORER, Nucleic Acids Res., 1979 7, 1067; for a 3 ml/mn flow rate, elution is effected according to a linear gradient starting from 2% of acetonitrile (pure A) up to 7% of acetonitrile (50% of A/ 50% of B) in 15 mn time, followed by a level of 12% of acetonitrile during 5 mn; the retention times are given with respect to injection.

the calf spleen phosphodiesterase (2 mg suspended in ammonium phosphate solution, pH ≈ 6) were supplied by Boehringer Mannheim (RFA).

Di-O-benzoyl-3,5 di-O-acetyl-1,2 D-xylofurannose 11

To an ice-cooled solution consisting of acetic acid (260 ml) and acetic anhydrid (64 ml), containing 49.5 g of compound 5 (*), 22 ml of concentrated sulfuric acid are added (for half an hour) drop by drop and under magnetic stirring. The resulting mixture is stirred at room temperature during 12 hours, then poured onto 700 ml of iced water and finally extracted with three times 300 ml of chloroform. The organic phases are first washed in water, then with a 5% sodium carbonate solution, and finally again with water (three times 150 ml for each washing). The chloroformic solution is dried on sodium sulphate, filtrated and evaporated under reduced pressure. The residue is redissolved in 500 ml of ethanol 95 and treated with animal charcoal; after filtration, evaporation under reduced pressure and successive coevaporations with toluene (three times 100 ml) and carbon tetrachloride (twice 100 ml) the anomeric compound 11 is obtained with a yield of 54 g (98%) in the form of a pale yellow sirup, pure enough to be directly used in condensation reactions: ccm, RF=0.21 (eluent, ether cyclohexane: 1—1, v/v NMR (deuteriochloroform) $\delta$ ppm: 6.28 (s, 1H, H-1 $\beta$) 5,55 (d,1H, H-1 $\alpha$; $J_{1,2}$=4.5 Hz).

(*) B. R. BAKER et R. E. SCHAUB, *J. Amer. Chem. Soc.*, 1955, 77, 5900.

The 11-$\alpha$ anomer is crystallized in ethanol; F=108°-109° C.

Analysis: Calculated for $C_{23}H_{22}O_9$(442.41): C, 62.44; H, 5.01. found: C, 62.37; H, 5.02.

Di-O-benzoyl-3', 5' O-acetyl-2'$\beta$-D-xylofurannosyl-9 adenine 12

To a solution of 20.27 mg (45.8 mmoles of compound 11 in 900 ml of anhydrous acetonitrile, 6.05 g (46 mmoles) of adenine are added. 10.5 ml of stannous tetrachloride are added to the resulting suspension in 300 ml of the same solvent. The reaction mixture, which becomes absolutely clear after 30 minutes, is left under stirring for 15 hours in a dry place; it is then concentrated to a 210 ml volume and 26.6 g of sodium hydrogenocarbonate and 90 ml of water are successively introduced. When carbonic gas has completely disappeared, the mixture is evaporated under reduced pressure and the resulting gum is extracted with three times 300 ml of boiling chloroform; the organic phases are pooled, dried on sodium sulphate, filtrated and evaporated under reduced pressure, thus resulting into a gum. A column chromatography (eluent dichloromethane-methanol: 9.6-0.4 v/v) enables compound 12 to be collected with a yield of 16.5 g (70%), the latter crystallizes in ether; ccm, Rf=0.31 (eluent dichloromethane-methanol: 9.3-0.7, v/v) F=108°-110° C.;

Analysis: calculated for: $C_{26}H_{23}N_5O_7$(517.48): C, 60.34; H, 4.48; N, 13.54. found: C, 60.35; H, 4.42; N; 12.9.

$\beta$-D-xylofurannosyl-9 adenine 13

3.81 g of compound 12 are dissolved in 30 ml of sodium methylate methanolic solution 1N. After 1 hour of stirring at room temperature, the compound is evaporated under dry conditions, redissolved in 150 ml of water and rapidly neutralized with Dowex 50 resin (pyridinium form); after filtration and extraction with ether of the methyl benzoate, the aqueous phase is evaporated under vacuum; by re-adding methanol, compound 13 crystallizes with half a molecule of water; it is obtained with a yield of 1.58 g (78%).

The physical characteristics of this compound 13 are in every point identical to those of $\beta$-D-xylofurannosyl-9 adenine obtained.

Di-0-benzoyl-3',5'$\beta$-D-xylofurannosyl-9 adenine 14

2.82 hydrated hydrazine (58.0 moles . 3 eq.) are added to a solution of 10 g. (19.3 mmoles, 1 eq.) of compound 12 in 168 ml of an acid acetic-pyridine mixture: 1-4 v/v.

After 20 hours of stirring at room temperature, 47 ml of acetone are added and the stirring is carried on for two hours. The mixture is thereafter concentrated under reduced pressure and redissolved within 300 ml of chloroform. The resulting chloroformic solution is washed first with water, then with a solution saturated with sodium hydrogenocarbonate, and finally again with water (twice 150 ml for each washing).

The organic phase is dried on sodium sulphate, filtrated and dry evaporated; after three coevaporations with a toluenethanol: 4-1, v/v, 8.36 g of an orange-coloured foam are obtained. A column chromatography (eluent, dichloromethane-methanol: 9.7-0.3, v/v) enables the compound 14 to be obtained with a yield of 7.54 g (82%).

This compound 14 may be precipitated in isopropylic ether; ccm, Rf: 0.28 (eluent, chloroform-methanol: 9-1, v/v); F: 94-165° C. (decomposition).

Analysis:

Calculated for: $C_{24}H_{21}N_5O_6$(475.45): C, 60.63; H, 4.45, N, 14.73 . found: C, 60.41; H, 4.68; N, 14.27.

Di-0-benzoyl-3', 5'0-tertiobutyldimethylsilyl-2'$\beta$-xylofurannosyl-9 adenine 15

Within 18 ml of anhydric dimethylformamide, 6 g (12.6 mmoles, 1 eq.) of compound 14, 2.06 g (30, 2 mmoles, 2.4 eq) of imidazole and 2.29 g (15.2 mmoles, 1.2 eq) of tertiobutyldimethylsilyle chloride are dissolved successively in this order. After 7 hours of stirring at room temperature, this solution is poured onto 100 ml of iced water and extraction is carried out with three times 100 ml dichloromethane; the organic phases are collected, dried on sodium sulphate, filtrated and evaporated under reduced pressure. The resulting oil is extracted at 40° C. under vacuum (about $10^{-2}$ mm of Hg) for 6 hours, so as to clear off the maximum dimethylformamide. A column chromatography (eluent dichloromethane-methanol: 9.9-0.1, v/v) of the gum obtained enables the compound 15 to be collected with a yield of 5.83 g (78%); it crystallizes in an ether-petroleum ether mixture; ccm, Rf=0.55 (eluent, chloroform-ethanol: 9-1, v/v); F=170°-171° C.

Analysis:
Calculated for: $C_{30}H_{35}N_5O_6Si$ (589.71):C, 61.10; H, 5.98; N, 11.98; Si, 4.76. found: C, 61.36; H, 5.79; N, 11.70; Si, 4.7

0-tertiobutyldimethylsilyl-2'$\beta$--D-xylofurannosyl-9 adenine 16

4.5 g of compound 15 are dissolved in 22 ml of a methanolic solution of sodium methylate 1N; the mixture is stirred for 30 minutes at room temperature, then evaporated under reduced pressure, redissolved within 50 ml of water and rapidly neutralized with Dowex 50 resin (pyridinium form). After filtration and evporation, the residue is coevaporated twice with 10 ml of ethanal 100, then chromatographied on a column (eluent, dichloromethane-methanol: 9.2–0.8, v/v); compound 16 is obtained with a yield of 2.18 g (75%); it crystallizes in ether; ccm, Rf=0.15 (eluent chloroform/methanol: 9-1, v/v); F: 127°–129° C.

Analysis: Calculated for: $C_{16}H_{27}N_5O_4Si$ (381.51): C, 50.37 H, 7.14; H, 18.36; Si 7.36. found: C, 50.02; H, 7.20; N, 18.10; Si 7.1.

0-monomethoxytrityl-5' 0-tertiobutyldimethylsilyl-2-$\beta$-D-oxylofurannosyl-9 adenine 17

A solution containing 7.75 g (20.3 mmoles, 1 eq) of compound 16 and a 8.17 g (26.5 mmoles, 1.3 eq) of monomethoxytrityle chloride within 280 ml of anhydrous pyridine is stirred for 20 hours in a dark and dry place. After addition of 130 ml of iced water, the reaction mixture is extracted with twice 200 ml of chloroform: the organic phase is dried on sodium sulphate, filtrated and evaporated under reduced pressure; the residue is three times evaporated with 50 ml of toluene and thereafter is chromatographied on a column (eluent, dichloromethane-methanol-trithylamine: 9.7–0.2–0.1) v/v). Compound 17 is obtained with a yield of 9.87 g (74%): it crystallizes in a mixture of ether and petroleum ether ccm, Rf=0.34 (eluent methanol -dichloromethane; 9.4–0.6 v/v); F: 103° C.

Analysis: Calculated for: $C_{36}H_{43}N_5O_5Si$ (653.83): C, 66.13; H, 6.63; N, 10.17; Si, 4.30. found: C.65.95; H, 6.46; N, 10.40; Si 4.1.

N-0-dibenzoyl-6,3' 0-monoethoxytrityl-5' 0-tertiobutyldimethysly-2' $\beta$D-xylofurannosyl-9 adenine 18

A solution containing 9.06 g (13.9 mmoles, 1 eq) of compound 17, 0.90 g (7.37 mmoles, 0.53 eq) of N,N-dimethylamino-4 pyridine and 6.92 g (30.6 mmoles, 2.2 eq) of benzolc anhydride in 200 ml of anhydrous pyridine is brought to reflex for 12 hours. After cooling and evaporating under reduced pressure, the residue is dissolved in 500 ml of chloroform; the resulting solution is successively washed with a saturated solution of sodium hydrogenocarbonate and with water (twice 300 ml for each washing). The organic phase is then dried on sodium sulphate, filtrated an evaporated under reduced pressure. After a chromatography on a column (eluent chloroform-ethylacetate-triethylamine: 9.75–0.2–0.05, v/v) the compound 18 is obtained in the form of a foam with a yield of 9.71 g (81%): ccm, Rf: 0.35 (eluent chloroformethyl acetate: 9-1, v/v; F: 77°–79° C.)

N-0-dibenzoyl-6,3' 0-monomethoxytrityl-5'$\beta$-D-xylofurannosyl-9-adenine 1

8.4 g of compound 18 are dissolved in 48 ml of a 0.5 N solution of tetrabutylammonium fluoride in tetrahydrofuranne; after 4 hours of stirring at room temperature, the solution is evaporated under reduced pressure and the residue is subjected to a column chromatography (eluent, dichloromethane-methanoltriethylamine 9.8–0.15–0.05, v/v); the compound 18 is obtained with a yield of 6.19 g (85%). It is precipitated in a mixture of carbon tetrachloride and diisopropylic ether; ccm Rf: 0.23 (eluent dichloromethane-methanol: 9.6–0.4, v/v); F: 135°–140° C. (decomposition).

Analysis: Calculated for: $C_{44}H_{37}N_5O_7$, 1/3 $CCl_4$ 1/3 $C_4H_{10}O$: C, 66.79; H, 5.04; N, 8.40 . found: C, 66.48; H, 5.00; N, 8.52.

N-0-tribenzoyl-6,2',3'$\beta$-D-xylofurannosyl-9-adenine 2

Method A

A solution containing 2.96 g (3.96 mmoles, 1 eq) of compound 1, 0.11 g (0.9 mmole, 0.23 eq) of N,N-dimethylamino-4 pyridine and 0.94 g (4.2 mmoles, 1.06 eq) of benzolc anhydride in 40 ml of anhydrous pyridine is brought to reflux for 12 hours. The reaction mixture is then treated according to the same process as that of the 18 synthesis. After a chromatography on a column (eluent, dichloromethane-methanol: 9.88–0.12, v/v) compound 20, which is pure enough to be directly used in the next step, is obtained with a yield of 2.87 g (85%); ccm, Rf=0.36 (eluent, dichlormethane-methanol: 9.8–0.2, v/v).

The 2.87 g of compound 20 are then dissolved in 28 ml of a chloroform-methanol mixture: 7-3, v/v, containing 2% of paratoluene sulfonic acid. The resulting solution is stirred at room temperature for 1 hour 30, then diluted with 200 ml of chloroform. After successive washings with a 5% sodium hydrogenocarbonate solution and with water (150 ml of each ), the chlorformic phase is dried over sodium sulfate, filtrated and evaporated under reduced pressure. A column chromatography (eluent dichloromethane-methanol: 9.8–0.2, v/v) enables compound 2 to be obtained with a yield of 1.25 g (64% with respect to 20; 55% with respect to 1). Compound 2 crystallizes in ethanol; ccm, Rf=0.28 (eluent, dichloromethane-methanol): 9.6–0.4, v/v); F: 131°–135° C.

Analysis: Calculated for: $C_{31}H_{25}N_5O_7$, $H_2O$ (597.57): C, 62.30; H 4.55; N 11.72. found: C 62.51; H 4.57; N 11.71.

Method B 1.0 g (3.6 mmoles, 1 eq) of compound 13 is dissolved in 50 ml of anhydrous ethanol. In order to eliminate the crystallization water, the resulting solution is evaporated under reduced pressure, then successively coevaporated with anhydrous ethanol and anhydrous pyridine (twich 50 ml in each case). 70 ml of a dimethyl formamide-pyridine mixture: 1-1, v/v and 1.42 g (4.6 mmoles, 1.3 eq) of monomethoxytrityle chloride are then added. After 36 hours of stirring in a dark and dry place, the reaction mixture is treated according to the same process as that of the 17 synthesis. A chromatography on a column (eluent, dichloromethane-methanol triethylamine: 9.4–0.5–0.1, v/v) enables 0-monomethoxytrityl-5'-$\beta$-D-xylofurannosyl-9 adenine 19 to be obtained with a yield of 1.38 g (71%); this compound 19 crystallizes in a mixture of ethyl acetate and of cyclohexane; ccm, Rf=0.26 (eluent, dichloromethane-methanol-triethylamine: 8.9-1-0.1, v/v): F: 129°-131° C.

The 1.38 g (2.6 mmoles, 1 eq) of compound 19 are then dissolved in 20 ml of anhydrous pyridine; to this solution, 0.22 g (1.8 mmoles, 0.7 eq) of N,N dimethylamino-4 pyridine and 1.82 g (8.0 mmoles, 3.1 eq of benzoic acid are added. The reaction mixture is brought to reflux for 12 hours and then treated according to the same process as that of the synthesis of compound 18. After purification on a column, the 0-monomethoxytrityl-5′ N,0-tribenzoyl-6,2′, 3′β-D-xylofuranosyl adenine 20 is thus obtained with a yield of 1.83 g (83%).

The transformation of this compound 20 into the desired 2 synthon may be carried out according to the same process as the one described in method A.

0-chlorophenylphosphate-2′ (0-monomethoxytrityl-5′N, 0-dibenzoyl-6,3′β-D xylofurannosyl-9 adenine) of triethylammonium 22

A solution of o-clorophenylphosphorodi-(triazol-1,2,4 ide) (W. T. MARKIEWICZ, E. BIALA, R. W. ADAMIAK, K. GRZESKOWIAK, R. KIERZEK, A. KRASZEWSKI, J. STAWINSKI and WIERWIOROWSKI, *Nucleic Acids Res.*, Symposium Series N°7, 1980, 115)-(J. B. CHATTOPADHYAYA & C. B. REESE, *Tetrahedrom Lett.* 1979, 5059)-(J. B. CHATTOPADHYAYA & C. B. REESE, *Tetrahedron Lett.*, 1979, 5059) is prepared in situ within 13.6 ml of anhydrous acetonitrile, starting from 1.20 g (17.7 mmoles) of triazole 1,2,4 of 1.67 (6.8 mmoles) of o-chlorophenyl phosphorodichloridate and 1.38 g (13.6 mmoles) of triethylamine.

After 15 minutes of stirring at room temperature, a solution of 2.1 g (2.8 mmoles) of compound 1 in 13.5 ml of anhydrous pyridine is then added and the stirring is carried on for 20 minutes a solution of 1.71 g (16.9 mmoles) of triethylamine and of 0.8 ml (43.9 mmoles) of water in 5.4 ml of pyridine is then added and subjected to stirring for 15 minutes. The reaction mixture is then poured into 350 ml of an aqueous solution saturated with sodium hydrogenocarbonate and then extracted with chloroform (4 times 80 ml). The pooled chloroformic phases are washed with an aqueous solution saturated with sodium hydrogenocarbonate (twice 150 ml) and then with water (twice 200 ml). Th organic phase is dried on sodium sulphate, filtrated, evaporated under reduced pressure, redissolved in a minimum quantity of chloroform and coevaporated three times with toluene.

The obtained foam is redissolved in 15 ml of chloroform and dripped into 450 ml of petroleum ether under high stirring. The compound 22 is obtained in the form of a precipitate which is settled and then dried by drier; the yield of 22 reaches 2.8 g (96%); ccm, Rf=0 (eluent chloroform-methanol: 9.6-0.4, v/v); 0.37 (eluent chloroform methanol: 8-2, v/v).

N-0-dibenzoyl-6.3′βD-xylofurannosyl-9 adenyl)-2′, (N,0-tribenzoyl-6,2′,3′, β-D-xylofurannosyl-9 adenyl)5′, (o-chlorophenyl)phosphate 24

To an anhydrous solution of pyridine (7.5 ml) containing 1.6 g (1.54 mmoles) of phosphodiester 22 and 0.76 g (1.31 mmoles) of synthon 2, 1.12 g (3.9 mmoles) of mesitylenesulfonyl-1 nitro-3 triazole-1,2 4 are added (S. S. JONES, B. RAYNER, C. B. REESE, A. UBASAWA & M. URASAWA, Tetrahedron, 1980, 36, 3075). The solution is stirred at room temperature for 20 minutes; then 1.5 ml of an aqueous solution saturated with sodium hydrogenocarbonate is added and the stirring is carried on for 15 minutes. At the end of this time, the mixture is poured into 150 ml of aqueous saturated $NaHCO_3$ and the products are extracted with chloroform (4 times 50 ml). The pooled organic phases are washed with water (once 80 ml), dried over sodium sulphate, filtrated and evaporated under reduced pressure. The residue is coevaporated three times with toluene in order to eliminate the ultimate traces of pyridine.

A thin layer chromatography (ccm) (eluent chloroform-methanol: 9.6-0.4, v/v) of this crude product shows that the totally protected dimer 23 thus obtained (Rf: 0.57) is pure enough to be directly used in the next step.

This residue is then dissolved in 26 ml of a chloroform-methanol mixture 7.3, v/v, containing 2% of paratoluene sulfonic acid. The resulting solution is stirred at room temperature for 60 minutes and then poured into 120 ml of aqueous saturated $NaHCO_3$, and the products are extracted with chloroform (4 times 60 ml). The organic phases are pooled, washed with water (once 100 ml), dried over sodium sulphate, filtrated and then evaporated under reduced pressure. A chromatography on a column (eluent, chloroform-methanol: 9.7-0.3, v/v) enables the detrylated dimer 24 to be obtained. The latter is isolated in the form of a white powder by precipitation in petroleum ether with a yield of 1.10 g (70% with respect to 2): ccm, Rf-0.24 and 0.17: two diastereoisomers (chloroform-methanol eluent: 9.6-0.4 v/v); 31 P-NMR (deuteriochloroform), δppm: −8.06 and −8.23.

Fully protected trinucleoside diphosphate 28

To a solution of anhydrous pyridine (5ml) containing 0.81 g (0.78 mmoles) of phosphodiester 22 and of 0.86 g (0.70 mmoles) of the detriylated dimer 24, 0.57 g (1.96 mmoles) of MSNT is added. The solution is stirred at room temperature for 20 minutes; then 1 ml of an aqueous solution saturated with $NaHCO_3$ is added and the stirring is carried on for 15 minutes. At the end of this time the mixture is poured into 80 ml of aqueous saturated $NaHCO_3$ is added and the stirring is carried on for 15 minutes. At the end of this time the mixture is poured into 80 ml of aqueous saturated $NaHCO_3$ and the products are extracted with chloroform (4 times 40 ml). The pooled organic phases are washed with water (once 60 ml), dried over sodium sulphate, filtrated and evaporated under reduced pressure. The residue is coevaporated three times with toluene and then subjected to a chromatography on column (eluent chloroform-methanol: 9.85-0.15, v/v): the concerned fractions are pooled and evaporated under reduced pressure; the trimer 28 thus obtained is precipitated in petroleum ether in the form of a white powder: yield 1.3 g (86% with respect to 24); ccm, Rf: 0.42; 0.37; 0.33 and 0.28: four diastereoisomers (eluent chloroform-methanol: 9.6-0.4, v/v); −P-MNR (deuteriochloroform), δppm: −8.00; −8.06; −8.17;−8.51.

Xyloadenylyl-(2′→5′)-xyloadenylyl-2′→5′) xyloadenosine 29

Deblocking

A solution of 25 mg (11.6 $10^{-3}$ mmoles) of the totally protected trimer 28, 66, 4 mg (0.4 mmoles) of nitro-4 synbenzaldoxime and 46.1 mg (0.4 mmoles) of N,N,N,N-tetramethyl-1,1,3,3 guanidine, in a water-dioxane mixture (1/1, v/v: 0.8 ml) is stirred for 5 hours at room temperature. At the end of this time, 23 mg (0.2 mmoles) of N,N,N,N-tetramethyl-1,1,3,3 guanidine are added and the solution is stirred for 16 additional hours.

After evaporation under reduced pressure, 4 ml of concentrated ammoniac (20%) are added to the gum thus obtained and the resulting solution is maintained in a tightly closed tube for 20 hours at 40° C.

This solution is then dry evaporated; the residue is coevaporated twice with water, then dissolved in 5 ml of a 80% aqueous acetic acid. The solution thus formed is stirred at room temperature for 4 hours, and then successively washed with chloroform (8 times 12 ml) and ethylic ether (4 times 12 ml).

The aqueous phase is evaporated under reduced pressure and then coevaporated with water to neutrality.

Purification

The precedingly obtained residue is subjected to a chromatography on a column (1.5×15 cm) of DEAE-Sephadex A-25 ($HCO_3^-$ form). The elution is carried out with a triethylammonium hydrogenocarbonate aqueous buffer, (pH 7.5), according to a linear gradient of from $2 \cdot 10^{-3}$ M to 0.5 M. 6 ml fractions are collected; those containing trimer 29 are pooled, evaporated under reduced pressure, coevaporated five times with water and then lyophilized. The desired trimer 29 is thus obtained with a yield of 82%.

Purity control ccm: Rf=0.28 (eluent, ammonium acetate(1N)-ethanol: 2-8, v/v); 0.38 (eluent, isopropanol-concentrated ammoniac-water 7-2-1, v/v; 0.40 (eluent, isopropanol-concentrated ammoniac-water: 7-1-2, v/v).

HPLC retention time: 13. 8 minutes.

To a solution of trimer 29 (3 units $A_{254}$) in 25 μl of water, 20 μl of a cocktail (prepared by mixing 230 μl of water, 60 μl of Tween 80, 50 μl of EDTA 0.1 M, 60 μl of a molar solution of $KH_2PO_4$ reduced to a pH 6.1 with 1 M sodium hydroxyde and then 80 μl of water and 3 μl of the spleen rate phosphodiesterase commercial solution are added. The obtained solution is incubated at 37° C. for 16 hours and then heated up to 80° C. for 2 minutes. The HPLC analysis of the digestion crude products shows but one peak corresponding to trimer 29.

Preparation of the polyphosphated oligonucleotides according to the invention For preparing oligonucleotides according to the invention, wherein one at least of the terminal nucleosidic units are linked to one or more phosphate groups (i.e. the 5' carbon atom of the "first" nucleosidic unit is engaged in a linking with a phosphate group and/or the 2' carbon atom of the "last" nucleosidic unit is engaged in a linking with a phosphate group) for instance three phosphate groups, it is possible to resort to conventional methods.

By way of example, for preparing oligonucleotides of the invention wherein the "first" group, as above defined, comprises one to three phosphate groups, on the 5' carbon, it is possible to use method A or B below described.

METHOD A

In the compound of formula 1:

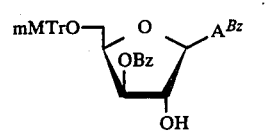

the 5' monomethoxytrityl group is eliminated, for instance with 2% p-toluenesulfonic acid in a mixture of chloroform-methanol, to obtain compound of formula 30:

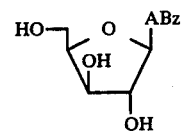

Then 2,2,2-trichloroethyl-phosphoromorpholine-chloridate is reacted on to compound 30, in the presence of 1-methylimidazole, to yield the compound of formula 31:

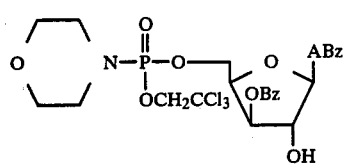

Compound 31 is then liable to be involved in the last condensation step of the reactions which have been already desired.

It is advantageously used in the above described process, instead of compound 22, for obtaining oligonucleotides according to the invention, wherein:

the 5' carbon atom of the first nucleosidic unit is engaged in a linking with the 2,2,2-trichloroethyl-morpholinophosphonate group of formula:

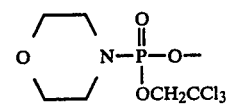

and are "fully protected".

In the following of the description, the expression "fully protected" means that:

all the optional 3' hydroxy groups, the optional 2' hydroxy group of the last nucleosidic unit, the exocyclic amino functions of the purine or pyrimidine bases, as above defined, are protected by protective baso labile groups, preferably benzoyl groups;

all the hydroxy group of the internucleosidic bonds are protected, for instance by the orthochlorophenyl group.

Said oligonucleotides:

are then reacted with the 2,4,6-triisopropylbenzene-sulfonic acid, in pyridine, in the presence of activated Zn, to yield oligonucleotides wherein the 2,2,2-trichloroethyl-morpholinophosphonate group in the 5' position is transformed into:

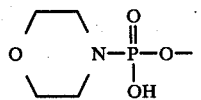

These oligonucleotides are further converted into:
the corresponding 5' monophosphate "fully protected" oligonucleotides by ammonolyse followed by an acid treatment;
the corresponding 5' diphosphate "fully protected" oligonucleotides by reaction with tributylammonium in dimethylformamide;
the corresponding 5' triphosphate "fully protected" oligonucleotides by reaction with bis-tributylammonium diphosphate in dimethyl formamide.

The respective 5' monophosphate, 5' diphosphate, 5' triphosphate "fully protected" oligonucleotides thus obtained are then deprotected (with respect to their optional 3' hydroxy groups, the optional 2' hydroxy group of the last nucleosidic unit, the amine functions of the bases, the hydroxy groups of the internucleosidic bonds), for instance by means of p-nitrobenzaldoximate of tetramethyl guanidinium, followed by treatment with 20% aqueous ammoniac, for instance in a similar process as the one described for the deprotection of compound 28.

By way of example, it is possible to resort to the method described by J. A. J. DEN HARTOG, R. A. WIJNANDS and J. H. VAN BOOM, "Chemical synthesis of p-p-p A2' p5' A2' p5' A, an interferon iduced inhibitor of protein synthesis and some functional analogs", J. Org. Chem. 1981, 46, 2 242-2 251.

METHOD B

Starting from an oligonucleotide according to the invention, wherein:
the 5' hydroxy group is protected, by an acido labile protective group, for instance by a monomethoxytrityl group;
all the optional 3' hydroxy group, the optional 2' hydroxy group of the last nucleosidic unit, the amine functions of the bases, are protected, with baso labile protective groups, particularly with benzoyl groups;
all the hydroxy groups of the internucleosidic bonds are protected, for instance with the orthoclorophenyl groups; the monomethoxytrityl group is eliminated, for instance by 20% p-toluenesulfonic acid, such as it has been already described.

The oligonucleotide thus obtained:
is reacted on to bis-(2,2,2-trichloroethyl) phosphorochloridite of formula: $(CCl_3-CH_2)_2$-PCl to yield an oligonucleotide wherein the 5' carbon atom of the first nucleosidic unit is linked to a $(CCl_3-CH_2)_2$-P-O group;
and the phosphorus of the above represented group is the oxydized, for instance by $I_2$, with ether and aqueous $NaHCO_3$, to yield an oligonucleotide wherein the 5' carbon atom of the first nucleosidic unit is linked to a

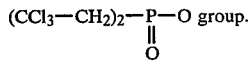

The trichloroethyl groups linked to the phosphorus atom, as above represented, are then eliminated, for instance with activated Zn/Cu, in a mixture of dimethylformamide-acetylacetone.

The oligonucleotide obtained is "fully protected" as above defined in which the 5' carbon atom of the first nucleosidic unit is linked to one phosphate group.

By way of example, it is possible to resort to the process described by J. IMAI and P. F. TORRENCE, "Bis-(2,2,2-trichloroethyl)phosphorochloridite as reagent for the phosphorylation of oligonucleotides. Preparation of 5' phosphorylated 2',5' oligoadenylate", J. Org. Chem., 1981, 46, 4 015-4 021.

All the protective groups of the oligonucleotide are then eliminated, for instance according to what has been previously described and the 5' monophosphate oligonucleotide obtained is then transformed into the corresponding 5' diphosphate and 5' triphosphate, by reaction of imidazolidate with the respective monophosphate or pyrophosphate anion.

For preparing an oligonucleotide according to the invention, wherein the "last" nucleosidic group as above defined comprises one to three phosphate groups on the 2' carbon atom, it is possible to resort to the above described methods (A or B), in which the 2' carbon atom of the last nucleosidic unit, is appropriately brought into play, in ways similar to the ones described for 5' carbon atom of the first nucleosidic unit.

It is understood that the above described alternatives relative to the obtention of oligonucleotides in which one at least of the terminal nucleosidic units is linked to one or more several phosphate groups can be used whatever the terminal nucleosidic units contemplated hereabove, in so far as the protective groups are chosen appropriately with respect to the terminal nucleosidic unit which is to be engaged into the polyphosphate linkage.

Physicochemical properties of the trimer of β-D-xylofurannosyl-9-adenine with 2'→5' internucleotidic bonds The purity of the trimer of formula 29, is checked:
by thin layer chromatography hereafter designated by ccm;
by high pressure liquid chromatography (HPL);
by enzymatic digestion.

This oligonucleotide turns out to be totally resistant to phosphodiesterase of calf spleen.

The study of the physicochemical properties of trimer 29 consists on the one hand in determining the optical characteristics, and on the other hand in the analysis of the NMR spectrum.

Optical characteristics

They have been studied with respect to the natural "(2'→5')A3 core".

This one has been prepared by an enzymatic route from ATP, and by using, as a source of 2',5' oligoadenylate synthetase, an homogenate of HELA cells treated by interferon α (J. MARTI, Laboratoire de Biochimie des Protéines, U. S. T. L.).

The hypochromicity and the value of ε of each trimer have been determined after enzymatic hydrolysis at pH 8.4.

For the maximum ε of xylo and ribonucleosides and nucleotides, the value which has been used is 15 400 (λ max: 259 nm).

The results obtained are gathered in the following table.

|  | λ max | ε 257 nm | Hypochromicity 259 nm |
|---|---|---|---|
| 2' → 5' A natural | 257 nm | 35 100 | 24% |
| 2' → 5' XYLO A | 257 nm | 38 400 | 18% |

The hypochromic and hypsochromic aspects of UV absorption spectrum of these trimers comparatively to their constituents can be explained by a piling up of the bases along their chain.

Analysis of the NMR spectrum

A sample of the compound 29 has been transformed into its corresponding sodium salt by treatment with a cation ($Na^+$) exchange resin commercialized under DOWEX, then lyophilized three times in $D_2O$, after the pH was brought to 7.4. Its NMR spectrum of proton at 500 MHz has been recorded at 42° C., in a $D_2O$ solution, at a concentration of 4.5 mM and using an internal $D_2O$ lock.

Traces of chloride of tetramethyl ammonium (TMA Cl) has been added to the sample for internal reference (with trimethylsilyl-3-propanesulfonic acid, sodium salt, TMA Cl appears at 3.18 ppm).

Sodium salt of xyloadenylyl (2'→5') xyloadenylyl (2'→5')xyloadenosine NMR spectrum is represented in FIG. 1.

The chemical shiftings of its protons with respect to tetramethylammonium chloride as well as the values of coupling constants are gathered in the following table.

This analysis confirms the chemical structure and the purity of trimer which has been synthesized.

| FRAGMENT | PROTON | δ ppm (/TMA Cl) | J (Hz) |
|---|---|---|---|
| Ap— | 1' | 2,886 | 1',2' = 2,0 |
|  | 2' | 1,675 | 2',3' = 1.6; 2',P = 8,8 |
|  | 3' | 1,208 | 3',4' = 3,9 |
|  | 4' | 1,148 | 4',5' = 4,0 |
|  | 5' | 0,663 | 4',5" = 6,8 |
|  | 5" | 0,599 | 5',5" = −12,3 |
| —pAp— | 1' | 2,682 | 1',2' = 2,3 |
|  | 2' | 1,586 | 2',3' = 2,1; 2',P = 8,7 |
|  | 3' | 1,301 | 3',4' = 4,2 |
|  | 4' | 1,200* | 4',5' = 3,2; 4',P = 1,5* |
|  | 5' | 0,984 | 4',5" = 6,0; 5',P = 5,3 |
|  | 5" | 0,939 | 5',5" = −11,6; 5",P = 6,0 |
| —pA | 1' | 2,515 | 1',2' = 4,0 |
|  | 2' | 1,283 | 2',3' = 3,8 |
|  | 3' | 1,170 | 3',4' = 5,0 |
|  | 4' | 1,186* | 4',5' = 4,4* |
|  | 5' | 0,954 | 4',5" = 3,0; 5',P = 4,6 |
|  | 5" | 0,926 | 5',5" = −11,5; 5",P = 5,2 |
|  | **H-8 | 5,023 |  |
|  | H-2 | 5,016 |  |
|  | H-2 | 4,959 |  |
|  | H-2 | 4,951 |  |
|  | H-8 | 4,866 |  |
|  | H-8 | 4,807 |  |

*the exact determination is impossible because of the overlapping of signals
**Aromatic protons H-2 and H-8 have been distinguished by thier relaxation time ($T_1$)

The meaning of Ap-, -pAp-, -pA- is given below:

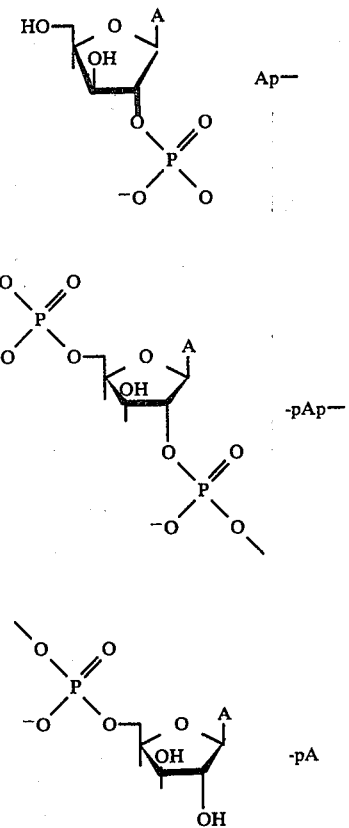

It is to be understood that the claims must be regarded as covering all equivalent final compounds as well as the processes for making said equivalents, it being then understood that the claims to the process must be regarded also as encompassing the corresponding process alternatives bringing into play the corresponding appropriate equivalents starting compounds to be used for finally obtaining the said final compounds.

The expression "equivalent final compounds" as termed hereabove aims at designating any final compound obtained which may distinguish from the final compounds defined in the claims by any minor chemical alterations of the molecule, readily ascertainable by the man skilled in the art, the effect of which is however not liable of affecting to a substantial extent the essential interferon-like properties of the unaltered molecules, of increased duration of activity, as detectable particularly by capability of endoribonucleases to recognize them and to build up with them an active complex and/or increased resistance to degradation by 2'-phosphodiesterases.

Among alterations of that kind liable of being contemplated by the man skilled in the art one may, merely by way of example, consider those liable of being brought to the bases associated with the xylose (or desoxyxylose) residues-or other osidic residues
  particularly the substitutes of deazadenine residues, such as 1-deazadenine-, 3-deazadenine- or 7-deazadenine-residues for part or all of the adenine residues in the several compounds which included them and which have been contemplated in the instant disclosure, or the linkage to some or all of the osidic groups of the adenine residues (or deazadenine residues) through a nitrogen atom at a different position in said adenine (or deazadenine residues), or limited substitutions on the free amino groups carried by said adenine or deazadenine residues by lower alkyl, say including from 1 to 5 carbon atoms as well as by phenyl or benzyl.

The invention further concerns the salts which the abovesaid oligonucleotides can form with bases, particularly inorganic or organic bases. Among salts of inorganic bases, sodium salts and potassium salts are preferred. Among organic salts, salts of amines, alkylamines or arylamines are preferred: particularly of secondary amines such as diethylamine, piperazine, or of tertiary amines, such as triethylamine, pyridine, methylpiperazine, etc... Among all these salts physiologically acceptable salts are preferred. The salts can be lyophilized.

The compounds of the invention have the most valuable biological properties, more particularly interferon-like properties, more specifically antiviral activity. They are capable of inhibiting DNA synthesis, particularly viral replication in cells and/or of degrading viral mARN, thus of inhibiting the biosynthesis of proteins, more particularly of viral proteins in cells infected by virus at nanomolar concentrations. They are stable and resist totally hydrolysis in the presence of 2', 5'-phosphodiesterases of mammal origin, particularly of claf spleen,. They even show increased resistance to as strong a phosphodiesterase as that originating from the snake venom known as *Crotalus durissus terrificus*. As a matter of fact, the oligomers according to the invention are hydrolized much slower in the presence of the last mentioned enzyme than are the natural 2'→5' oligo-adenylates. Particularly the xyloadenylyl (2'→5') xyloadenylyl (2'→5') xyloadenosine is hydrolized by the above phosphodiesterase at a rate four times less than the natural riboadenylyl (2'→5') riboadenylyl (2'→5') riboadenosine.

The oligonucleotides are thus valuable substitutes—particularly after the removal of the protection groups referred to hereabove—for interferon in its known uses, particularly biological uses. They may also be used, owing to the fact that they can be easily and reproduceably prepared, in a highly purified state, as biological reagents, particularly for use as comparative standards in biological qualitative and quantitative assays, in cell cultures, of interferon compounds or other interferon like substances or compositions containing such compounds or substances. These assays aim for instance at testing their capability of inhibiting virus replication in cell cultures or at testing related activities, such as those referred to in the publication mentioned hereafter. They may also be used as standards or references in the testing of the degree of increased resistance imparted to substrates for 2', 5'-phosphodiesterases with respect to degradation in the presence of such enzymes, as a result of chemical modification of these substrates, and/or the increased capability of said chemically-modified-substrates to activate in cells the endoribonucleases normally mediated by interferon and involved in the inhibition of viral DNA synthesis and viral protein synthesis.

As concerns the techniques of preferred assays where the compounds of the invention are useful as comparative standards, reference may be made to those disclosed by Knight M. et al (1980), "Radioimmune radiobinding and HPLC analysis of 2-5 A and related nucleotides from intact cells", Nature 288: 189-192;

Hovanessian A. G. et al (1979), "Increased nuclease activity in cells treated with pppA2'p5'A2'p5'A", Proc. Natl. Acad. Sci. USA, vol. 76, No. 7, pp. 3261-3265, July 1979;

Hovanessian et al, "Anticellular and Antiviral Effects of pppA(2'p5'A)n", Virology 101, pp. 81-90 (1980);

Kimchi et al, "Anti-mitogenic Function of Interferon-Induced (2'-5')Oligo(adenylate) and Growth-Related Variations in Enzymes that Synthesize", Eur. J. Biochem. 114, 5-10 (1981), FEBS 1981;

Baglioni C. et al, "Analogs of (2'-5')Oligo(A) Endonuclease activation and Inhibition of Protein Synthesis in Intact Cells", The Journal of Biological Chemistry, vol. 256, No. 7, Issue of April 10, pp. 3253-3257, 1981.

It is finally understood that all the subject matter disclosed in the publications identified in the instant disclosure is incorporated herein by reference, particularly in relation to any subject matter that may be liable of providing additional descriptional support to the full understanding of techniques which were already known from the prior art and which have been brought into play in the achievement of non essential parts of the invention.

We claim:

1. Oligonucleotide comprising a chain containing in turn n identical or different nucleosidic units, n being higher than 1, preferably not higher than 10, among which at least one of the nucleosidic units is constituted by xyloadenosine, these nucleosidic units being linked by a 2'→5' bond, comprising a linking group containing at least one phosphorus atom.

2. Oligonucleotide according to claim 1, wherein the first nucleosidic unit and/or the last nucleosidic unit is linked to phosphate groups, preferably 1 to 3 phosphate groups, these phosphate groups being optionally separated by one to 3 methylene groups.

3. Oligonucleotide according to claims 1 or 2, wherein the 2'→5' bond comprising a linking group containing at least one phosphorous atom is a phosphodiester bond, a phosphotriester bond or an alkylphosphonate bond.

4. Oligonucleotide according to claims 1, 2 or 3, wherein all the nucleosidic units derive from adenine.

5. Oligonucleotide according to claims 1, 2 or 3, wherein all the nucleosidic units derive from adenine and the 2'→5' bond comprising a linking group containing at least one phosphorous atoms is a phosphodiester bond, a phosphotriester bond or an alkylphosphonate bond.

6. Oligonucleotide according to claims 1, 2, 3, 4 or 5, comprising one D-$\beta$-xylofurannosyl-9-adenine of formula:

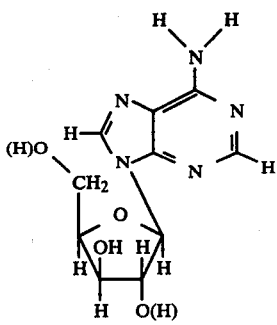

and the remaining (n-1) nucleosidic units derived from adenine are chosen from among:
ribofurannosyl-adenine,
arabinofurannosyl-adenine,
xylofurannosyl-adenine,
lyxofurannosyl-adenine,
ribopyrannosyl-adenine,
arabinopyrannosyl-adenine,
xylopyrannosyl-adenine,
lyxopyrannosyl-adenine,
desoxy-3'-ribofurannosyl-adenine,
desoxy-3'-arabinofurannosyl-adenine,
desoxy-3'-ribopyrannosyl-adenine,
desoxy-3'-arabinopyrannosyl-adenine, 7. Oligonucleotide according to claims 1, 2, 3, 4, 5 or 6, represented by the following formula:

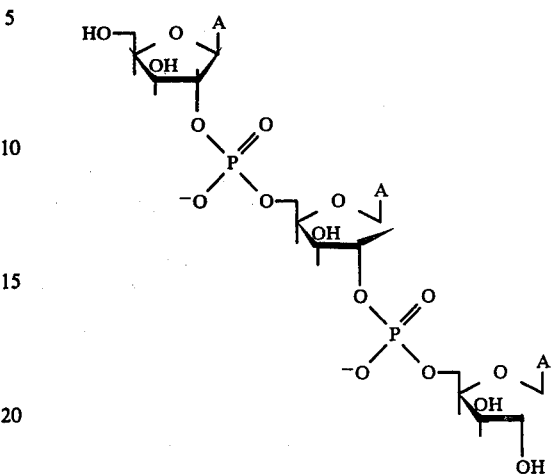

wherein A is adenine, its salt of quaternary ammonium, of triethyl-ammonium and its sodium salt.

* * * * *